United States Patent
Li et al.

(10) Patent No.: US 10,266,551 B2
(45) Date of Patent: *Apr. 23, 2019

(54) COMPOUNDS AND USES THEREOF FOR THE MODULATION OF HEMOGLOBIN

(71) Applicant: Global Blood Therapeutics, Inc., South San Francisco, CA (US)

(72) Inventors: Zhe Li, South San Francisco, CA (US); Qing Xu, South San Francisco, CA (US); Brian W. Metcalf, South San Francisco, CA (US); Stephen L. Gwaltney, II, South San Francisco, CA (US); Jason R. Harris, South San Francisco, CA (US); Calvin W. Yee, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/776,717

(22) PCT Filed: Mar. 10, 2014

(86) PCT No.: PCT/US2014/022736
§ 371 (c)(1),
(2) Date: Sep. 14, 2015

(87) PCT Pub. No.: WO2014/150258
PCT Pub. Date: Sep. 25, 2014

(65) Prior Publication Data
US 2016/0031904 A1 Feb. 4, 2016

Related U.S. Application Data

(63) Continuation-in-part of application No. 13/815,874, filed on Mar. 15, 2013, now Pat. No. 9,604,999.

(60) Provisional application No. 61/905,802, filed on Nov. 18, 2013.

(51) Int. Cl.
| C07D 498/08 | (2006.01) |
| C07D 491/107 | (2006.01) |
| C07D 403/04 | (2006.01) |
| C07D 401/04 | (2006.01) |
| C07D 213/74 | (2006.01) |

(52) U.S. Cl.
CPC ......... *C07D 498/08* (2013.01); *C07D 213/74* (2013.01); *C07D 401/04* (2013.01); *C07D 403/04* (2013.01); *C07D 491/107* (2013.01)

(58) Field of Classification Search
CPC ................ C07D 498/08; C07D 213/74; C07D 491/107; C07D 403/04; C07D 401/04
See application file for complete search history.

(56) References Cited

U.S. PATENT DOCUMENTS

| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Baiani |
| 5,266,582 A | 11/1993 | De Nanteuil et al. |
| 5,290,941 A | 3/1994 | Voiante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 11/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greenwald et al. |
| 6,627,646 B2 | 9/2003 | Bakale |
| 6,630,496 B1 | 10/2003 | Seehra et al. |
| 7,160,910 B2 | 1/2007 | Safo et al. |
| 7,411,083 B2 | 8/2008 | Gapalasamy et al. |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,248,199 B2 | 2/2016 | Metcalf et al. |
| 9,422,279 B2 | 8/2016 | Metcalf et al. |
| 9,447,071 B2 | 9/2016 | Li et al. |
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |

(Continued)

FOREIGN PATENT DOCUMENTS

| CA | 2720096 | 10/2009 |
| CN | 101113148 | 1/2008 |

(Continued)

OTHER PUBLICATIONS

Camille G. Wermuth, Molecular Variations Based on isosteric Replacements, The Practice of Medicinal chemistry, 1996, 203-232.*

(Continued)

*Primary Examiner* — Sarah Pihonak
*Assistant Examiner* — Jason Deck
(74) *Attorney, Agent, or Firm* — Sheppard Mullin Richter & Hampton LLP

(57) ABSTRACT

Provide herein are compounds and pharmaceutical compositions suitable as modulators of hemoglobin, methods and intermediates for their preparation, and methods for their use in treating disorders mediated by hemoglobin and disorders that would benefit from tissue and/or cellular oxygenation.

21 Claims, No Drawings

(56) References Cited

U.S. PATENT DOCUMENTS

| | | |
|---|---|---|
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Hague et al. |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann et al. |
| 2009/0163512 A1 | 6/2009 | Chen et al. |
| 2009/0312315 A1 | 12/2009 | Yamaguchi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2014/0004184 A1 | 1/2014 | Ashraf et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0303099 A1 | 3/2016 | Dufu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0332984 A1 | 11/2016 | Metcalf et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0327484 A1 | 11/2017 | Li et al. |
| 2018/0125789 A1 | 5/2018 | Dalziel et al. |

FOREIGN PATENT DOCUMENTS

| | | | | |
|---|---|---|---|---|
| CN | 102116772 | 7/2011 | | |
| DE | 2238734 | 2/1973 | | |
| DE | 2238628 | 3/1973 | | |
| DE | 2853765 | 8/1980 | | |
| DE | 2904829 | 8/1980 | | |
| DE | 226590 | 8/1985 | | |
| DE | 3503435 | 8/1985 | | |
| DE | 3431004 | 3/1986 | | |
| DE | 3704223 | 8/1987 | | |
| DE | 258226 | 7/1988 | | |
| DE | 276479 | 2/1990 | | |
| DE | 276480 | 2/1990 | | |
| DE | 3931954 | 3/1990 | | |
| DE | 4318550 | 12/1994 | | |
| DE | 4442050 | 5/1996 | | |
| EP | 10063 | 4/1980 | | |
| EP | 0054924 | 6/1982 | | |
| EP | 0054924 A2 * | 6/1982 | ............ | C07C 43/205 |
| EP | 236140 | 9/1987 | | |
| EP | 0268989 | 6/1988 | | |
| EP | 278686 | 8/1988 | | |
| EP | 291916 | 11/1988 | | |
| EP | 303465 | 2/1989 | | |
| EP | 336369 | 10/1989 | | |
| EP | 0348155 | 12/1989 | | |
| EP | 0365328 | 4/1990 | | |
| EP | 0401517 | 12/1990 | | |
| EP | 453210 | 10/1991 | | |
| EP | 462800 | 12/1991 | | |
| EP | 481802 | 4/1992 | | |
| EP | 498380 | 8/1992 | | |
| EP | 0528337 | 2/1993 | | |
| EP | 0542372 | 5/1993 | | |
| EP | 567133 | 10/1993 | | |
| EP | 0632036 | 1/1995 | | |
| EP | 0637586 | 2/1995 | | |
| EP | 0640609 | 3/1995 | | |
| EP | 0747393 | 12/1996 | | |
| EP | 2123637 | 11/2009 | | |
| EP | 2149545 | 3/2010 | | |
| EP | 2305625 | 6/2011 | | |
| FR | 2 217 016 | 9/1974 | | |
| FR | 2909379 | 6/2008 | | |
| GB | 1 409 865 | 10/1975 | | |
| GB | 1593417 | 7/1981 | | |
| IL | 64573 | 4/1985 | | |
| JP | 57-145844 | 6/1905 | | |
| JP | 59029667 | 2/1984 | | |
| JP | 61040236 | 2/1986 | | |
| JP | 63230687 | 9/1988 | | |
| JP | S-63258463 | 10/1988 | | |
| JP | 01190688 | 7/1989 | | |
| JP | 06041118 | 2/1994 | | |
| JP | 07025882 | 1/1995 | | |
| JP | 2002-523469 | 7/2002 | | |
| JP | 2002-528537 | 9/2002 | | |
| JP | 2003-075970 | 3/2003 | | |
| JP | 2003-513060 | 4/2003 | | |
| JP | 2006342115 | 12/2006 | | |
| JP | 2009203230 | 9/2009 | | |
| WO | WO 199119697 | 12/1991 | | |
| WO | WO 199202503 | 2/1992 | | |
| WO | WO 199317013 | 9/1993 | | |
| WO | WO 199401406 | 1/1994 | | |
| WO | WO 199514015 | 5/1995 | | |
| WO | WO 199521854 | 8/1995 | | |
| WO | WO 199611902 | 4/1996 | | |
| WO | WO-97/41120 | 11/1997 | | |
| WO | WO 199744306 | 11/1997 | | |
| WO | WO 199808818 | 3/1998 | | |
| WO | WO 199821199 | 5/1998 | | |
| WO | WO-99/29694 | 6/1999 | | |
| WO | WO 199943672 | 9/1999 | | |
| WO | WO 199947529 | 9/1999 | | |
| WO | WO 1999048490 | 9/1999 | | |
| WO | WO 199959978 | 11/1999 | | |
| WO | WO 199962908 | 12/1999 | | |
| WO | WO-00/12121 | 3/2000 | | |
| WO | WO-00/26202 | 5/2000 | | |
| WO | WO 2000035858 | 6/2000 | | |
| WO | WO 2000040564 | 7/2000 | | |
| WO | WO 200071123 A1 | 11/2000 | | |
| WO | WO-00/78746 | 12/2000 | | |

(56) References Cited

FOREIGN PATENT DOCUMENTS

| | | |
|---|---|---|
| WO | WO 2000075145 | 12/2000 |
| WO | WO 2001000612 | 1/2001 |
| WO | WO 2001019823 | 3/2001 |
| WO | WO-01/23383 | 4/2001 |
| WO | WO-01/32596 | 5/2001 |
| WO | WO 2001036375 | 5/2001 |
| WO | WO 2001057006 | 8/2001 |
| WO | WO 2001057044 | 8/2001 |
| WO | WO 2001062705 | 8/2001 |
| WO | WO 2001070663 | 9/2001 |
| WO | WO 2002000622 | 1/2002 |
| WO | WO 2002012235 | 2/2002 |
| WO | WO 2002024635 | 3/2002 |
| WO | WO 2002024679 | 3/2002 |
| WO | WO-02/053547 | 7/2002 |
| WO | WO 2002051849 | 7/2002 |
| WO | WO 2003051366 | 6/2003 |
| WO | WO 2003053368 | 7/2003 |
| WO | WO 2003101959 | 12/2003 |
| WO | WO-2004/014899 | 2/2004 |
| WO | WO 2004018430 | 3/2004 |
| WO | WO 2004024705 | 3/2004 |
| WO | WO 2004050030 | 6/2004 |
| WO | WO 2004056727 | 7/2004 |
| WO | WO 2004058790 | 7/2004 |
| WO | WO 2004087075 | 10/2004 |
| WO | WO-2004/111031 | 12/2004 |
| WO | WO-2005/047249 | 5/2005 |
| WO | WO 2005074513 | 8/2005 |
| WO | WO 2005077932 | 8/2005 |
| WO | WO-2005/086951 | 9/2005 |
| WO | WO 2005087766 | 9/2005 |
| WO | WO-2005/096337 | 10/2005 |
| WO | WO 2006011469 | 2/2006 |
| WO | WO-2006/065204 | 6/2006 |
| WO | WO 2006088173 | 8/2006 |
| WO | WO 2006103463 | 10/2006 |
| WO | WO 2006106711 | 10/2006 |
| WO | WO 2006116764 | 11/2006 |
| WO | WO-2006/003923 | 12/2006 |
| WO | WO 2007003962 | 1/2007 |
| WO | WO 2007009389 | 1/2007 |
| WO | WO 2007017267 | 2/2007 |
| WO | WO 2007047204 | 4/2007 |
| WO | WO-2007/061923 | 5/2007 |
| WO | WO 2007049675 | 5/2007 |
| WO | WO-2007/084914 | 7/2007 |
| WO | WO 2007117180 | 10/2007 |
| WO | WO 2008013414 | 1/2008 |
| WO | WO 2008016132 | 2/2008 |
| WO | WO-2008/029200 | 3/2008 |
| WO | WO-2008/041118 | 4/2008 |
| WO | WO-2008/051532 | 5/2008 |
| WO | WO 2008080391 | 5/2008 |
| WO | WO-2008/066145 | 6/2008 |
| WO | WO 2008081096 | 7/2008 |
| WO | WO 2008101682 | 8/2008 |
| WO | WO 2008116620 | 10/2008 |
| WO | WO 2009001214 | 12/2008 |
| WO | WO-2009/011850 | 1/2009 |
| WO | WO 2009050183 | 4/2009 |
| WO | WO-2009/128537 | 10/2009 |
| WO | WO 2009125606 | 10/2009 |
| WO | WO 2009130560 | 10/2009 |
| WO | WO 2009136889 | 11/2009 |
| WO | WO 2009146555 | 12/2009 |
| WO | WO-2010/031589 | 3/2010 |
| WO | WO-2010/056631 | 5/2010 |
| WO | WO 2010129055 | 11/2010 |
| WO | WO 2011033045 | 3/2011 |
| WO | WO-2011/088201 | 7/2011 |
| WO | WO 2011136459 | 11/2011 |
| WO | WO-2012/020060 | 2/2012 |
| WO | WO 2012138981 | 10/2012 |
| WO | WO 2012141228 | 10/2012 |
| WO | WO-2013/052803 | 4/2013 |
| WO | WO-2013/102145 | 7/2013 |
| WO | WO 2013102142 | 7/2013 |
| WO | WO 2013102145 | 7/2013 |
| WO | WO-2014/104384 | 7/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |
| WO | WO 2015/120133 | 8/2015 |
| WO | WO 2016/160755 | 10/2016 |
| WO | WO 2017/096230 | 6/2017 |

OTHER PUBLICATIONS

U.S. Appl. No. 13/815,735, filed Mar. 15, 2013, Xu.
U.S. Appl. No. 13/815,770, filed Mar. 15, 2015, Metcalf et al.
U.S. Appl. No. 13/815,776, filed Mar. 15, 2015, Xu.
U.S. Appl. No. 13/815,810, filed Mar. 15, 2015, Metcalf.
U.S. Appl. No. 13/815,872, filed Mar. 15, 2015, Metcalf.
U.S. Appl. No. 14/010,455, filed Aug. 26, 2015, Harris.
U.S. Appl. No. 14/207,289, filed Mar. 12, 2014, Li.
U.S. Appl. No. 14/216,346, filed Mar. 17, 2014, Li et al.
U.S. Appl. No. 14/662,145, filed Mar. 18, 2015, Metcalf et al.
U.S. Appl. No. 14/662,156, filed Mar. 18, 2015, Metcalf et al.
U.S. Appl. No. 14/776,603, filed Mar. 10, 2014, Metcalf et al.
U.S. Appl. No. 14/776,711, filed Mar. 10, 2014, Sinha et al.
U.S. Appl. No. 14/776,714, filed Mar. 10, 2013, Harris et al.
U.S. Appl. No. 14/776,715, filed Mar. 10, 2014, Li et al.
U.S. Appl. No. 14/776,717, filed Mar. 10, 2014, Li et al.
U.S. Appl. No. 14/776,723, filed Mar. 14, 2014, Metcalf et al.
U.S. Appl. No. 14/776,726, filed Mar. 10, 2014, Xu et al.
U.S. Appl. No. 14/791,017, filed Jul. 2, 2015, Xu et al.
U.S. Appl. No. 14/793,675, filed Jul. 7, 2015, Metcalf et al.
U.S. Appl. No. 14/809,151, filed Jul. 24, 2015, Dufu et al.
U.S. Appl. No. 14/836,869, filed Aug. 26, 2015, Xu et al.
Bacsa et al., "Novel products from Baylis-Hillman reactions of salicylaldehydes," South African Journal of Chemistry, 51(1): 47-54 (1998).
Ballet et al., "Novel selective human melanocortin-3 receptor ligands. Use of the 4-amino-1,2,4,5-tetrahydro-2-benzazepin-3-one (Aba) scaffold," Bioorganic & Medicinal Chemistry Letters, 17(9): 2492-2498 (2007).
Baxier et al., "Reductive aminations of carbonyl compounds with borohydride and borane reducing agents," Organic Reactions (Hoboken, NJ, United States), 59, including pp. 1-57 and 660-727, 125 pages (2002).
Beaumont et al., "Design of ester prodrugs to enhance oral absorption of poorly permeable compounds: challenges to the discovery scientist", Curr. Drug Metab., 4:461-85 (2003).
Beddell, "Substituted benzaldehydes designed to increase the oxygen affinity of human haemoglobin and inhibit the sickling of sickle erythrocytes," Br. J. Pharmac., 82:397-407 (1984).
Berge et al., "Pharmaceutical Salts," Journal of Pharmaceutical Science, 66:1-19 (1977).
Bode et al., "Novel synthesis and x-ray crystal structure of a coumarin derivative," South African Journal of Chemistry, 45(1):25-27 (1992).
Britton et al., "Structure-activity relationships of a series of benzothiophene-derived NPY Y1 antagonists: optimization of the C-2 side chain," Bioorganic & Medicinal Chemistry Letters 9(3):475-480 (1999).
Brown et al., "1,2-Dihydroisoquinolines—III. Dimerization," Tetrahedron, 22(8):2437-2443 (1966).
Ciganek, "The catalyzed alpha-hydroxyalkylation and alpha-aminoalkylation of activated olefins (the Morita-Baylis-Hillman reaction," Organic Reactions (Hoboken, NJ, United States), 51:201-267 and 342-350, 76 pages (1997).

(56) References Cited

OTHER PUBLICATIONS

Ding et al., "Crystal structure of bis(µ3-oxo)-bis[µ2-2-(2-formylphenoxy)acetato-O,O']-bis[µ2-2-(2-formylphenoxy)acetato-O,O']- octakis(n-butyl)tetratin(IV), Sn4O2(C9H7O4)4(C4H9)8," Zeitschrift fuer Kristallographie—New Crystal Structures, 226(1):31-32 (2011).
Elwahy, "Synthesis of new benzo-substituted macrocyclic ligands containing quinoxaline subunits," Tetrahedron, 56(6): 897-907 (2000).
Gadaginamath et al., "Synthesis and antibacterial activity of novel 1-butyl-2-phenoxy/2-phenylthio/2-aminomethyl-5-methoxyindole derivatives," Polish Journal of Chemistry, 71(7):923-928 (1997).
Gao et al., "A novel one-pot three-step synthesis of 2-(1-benzofuran-2-yl)quinoline-3-carboxylic acid derivatives," Journal of the Brazilian Chemical Society, 21(5):806-812 (2010).
Ghate et al., "Synthesis of vanillin ethers from 4-(bromomethyl) coumarins as anti-inflammatory agents," European Journal of Medicinal Chemistry, 38(3):297-302 (2003).
Grashey, "The nitro group as a 1,3-dipole in cycloadditions," Angewandte Chemie, 74:155 (1962).
Gunter et al., "Structural control of co-receptor binding in porphyrin-bipyridinium supramolecular assemblies," Journal of the Chemical Society, Perkin Transactions 1: Organic and Bio-Organic Chemistry, (12):1945-1958 (1998).
Hanmantgad et al., "Synthesis and pharmacological properties of some 4-(2'-benzo[b]furanyl)coumarins," Indian Journal of Chemistry, Section B: Organic Chemistry Including Medicinal Chemistry, 25B(7):779-781 (1986).
Heimbach et al., "2.2.1: Over-coming poor aqueous solubility of drugs for oral delivery," from Prodrugs: Challenges and Rewards, Part I, New York NY, Singer: AAPS Press, pp. 157-215 (2007).
Jarvest et al., "Discovery and optimisation of potent, selective, ethanolamine inhibitors of bacterial phenylalanyl tRNA synthetase," Bioorganic & Medicinal Chemistry Letters, 15(9):2305-2309 (2005).
Karche et al., "Electronic effects in migratory groups. [1,4]-versus [1,2]-rearrangement in rhodium carbenoid generated bicyclic oxonium ylides," Journal of Organic Chemistry, 66(19):6323-6332 (2001).
Katritzky et al., "Synthesis of 3-hydroxymethyl-2,3-dihydrobenzofurans and 3-hydroxymethylbenzofurans," ARKIVOC (Gainesville, FL, United States), (6):49-61 (2003).
Kaye et al. "DABCO-catalyzed reactions of salicylaldehydes with acrylate derivatives," Synthetic Communications: An International Journal for Rapid Communication of Synthetic Organic Chemistry, 26(11):2085-97 (1996).
Kaye et al., "Does the DABCO-catalysed reaction of 2-hydroxybenzaldehydes with methyl acrylate follow a Baylis-Hillman pathway?," Organic & Biomolecular Chemistry, 1(7):1133-1138 (2003).
Kessar et al., "An interesting application of photocyclisation in aporhoeadane alkaloid synthesis", Tetrahedron Letters, 28(44):5323-5326 (1987).
Kessar et al., "Synthesis of isoindolobenzazepines via photocyclization of N-(2-formylphenethyl)phthalimide derivatives," Indian Journal of Chemistry, 30B(11):999-1005 (1991).
Kise et al., "Electroreductive intramolecular coupling of phthalimides with aromatic aldehydes: application to the synthesis of lennoxamine," Journal of Organic Chemistry, 76(23):9856-9860 (2011).
Krow, Grant R., "Chapter 3, The Baeyer-Villiger oxidation of ketones and aldehydes," Organic Reactions, 43:251-353 and 775-808 (1993).
Lakkannavar et al., "4-[2'-Benzylideneanilino aryloxymethyl] coumarins E and Z isomers," Indian Journal of Heterocyclic Chemistry, 4(4):303-304 (1995).
Liu et al., "Synthesis of Double-Armed Benzo-15-crown-5 and Their Complexation Thermodynamics with Alkali Cations," Journal of Inclusion Phenomena and Macrocyclic Chemistry, 52(3-4):229-235 (2005).
Mahoney et al., "Functionalization of Csp3-H bond-Sc(OTf)3-catalyzed domino 1,5-hydride shift/cyclization/Friedel-Crafts acylation reaction of benzylidene Meldrum's acids," Tetrahedron Letters, 50(33):4706-4709 (2009).

Majhi et al, "An efficient synthesis of novel dibenzo-fused nine-membered oxacycles using a sequential Baylis-Hillman reaction and radical cyclization," Synthesis, (1):94-100 (2008).
Mantyla et al., "Synthesis, in vitro evaluation, and antileishmanial activity of water-soluble prodrugs of Buparvaquone", J. Med. Chem., 47:188-195 (2004).
McKay et al., "7,11,15,28-Tetrakis[(2-formylphenoxy)-methyl]-1,21,23,25-tetramethyl-resorcin[4]arene cavitand ethyl acetate clathrate at 173 K," Acta Crystallographica, Section E: Structure Reports Online, E65(4):0692-0693 (2009).
McKay et al., "Microwave-assisted synthesis of a new series of resorcin[4]arene cavitand-capped porphyrin capsules," Organic & Biomolecular Chemistry, 7(19):3958-3968 (2009).
Merlino et al., "Development of second generation amidinohydrazones, thio- and semicarbazones as *Trypanosoma cruzi*-inhibitors bearing benzofuroxan and benzimidazole 1,3-dioxide core scaffolds," Med. Chem. Commun., 1(3):216-228 (2010).
Mitra et al., "Synthesis and biological evaluation of dibenz[b,f][1,5]oxazocine derivatives for agonist activity at k-opioid receptor," European Journal of Medicinal Chemistry, 46(5):1713-1720 (2011).
Mulwad et al., "Synthesis and antimicrobial activity of [6'-methyl-4'-methoxy-2-oxo-2H-[1]-benzopyran)-2'',4''-dihydro-[1'',2'',4'']-triazol-3''-one and 3''-phenylthiazolidin-4''-one-phenoxymethyl derivatives of dipyranoquinoline," Pharmaceutical Chemistry Journal, 45(7):427-432 (2011).
Nagy et al., "Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling," Proc. Natl. Acad. Sci. USA, 90:6373-6376 (1994).
Neelima et al., "A novel annelation reaction: synthesis of 6H-Mbenzopyrano[4,3-b]quinolines," Chemistry & Industry (London, United Kingdom), (4):141-2 (1986).
Nnamani et al., "Pyridyl derivatives of benzaldehyde as potential antisickling agents", Chemistry & Biodiversity, 5:1762-1769 (2008).
Nogrady, Thomas, "4. Pro-drugs and soft drugs, Principles of Drug Design," from Medicinal Chemistry, a Biochemical Approach, Oxford University Press, New York, pp. 388-392, (1985).
Nonoyama et al., "Cyclometallation of 2-(2-pyridyl)benzo[b]furan and 1-(2-pyridyl and 2-pyrimidyl)indole with palladium(II) and rhodium(III). Structures of unexpectedly formed nitro palladium(II) complexes," Polyhedron, 18:533-543 (1999).
Nyerges et al., "Synthesis of indazole N-oxides via the 1,7-electrocyclization of azomethine ylides," Tetrahedron Letters, 42(30):5081-5083 (2001).
Nyerges et al., "Synthesis of indazole-N-oxides via the 1,7-electrocyclization of azomethine ylides" Tetrahedron, 60(44):9937-9944 (2004).
O'Reilly ert al., "Metal-phynoxy alkanoic acid interactions. XXV. The crystal structures of (2-formyl-6-methoxyphenoxy)acetic acid and its zinc(II) complex and there lithium, zinc(II) and cadmium(II) complexes of (2-cholorophenoxy)acetic acid," Australian Journal of Chemistry, 40(7):1147-1159 (1987).
Perez et al., "Preparation of new 1,2-disubstituted ferrocenyl stibine derivatives containing ether/thioether pendant arm from a quaternary ferrocenly ammonimun salt," Polyhedron, 28(14):3115-3119 (2009).
Perkins et al., "Magnanese(II), iron(II), and copper(II) complexes of an extended inherently chiral tris-bipyridl cage," Proceedings of the National Academy of Sciences of the United States of America, 103(3):532-537 (2006).
PUBCHEM CID 54009805, create date: Dec. 4, 2011, 3 pages (2011).
PUBCHEM CID 54883281, create date: Jan. 24, 2012, 3 pages (2012).
Remington's Pharaceutical Sciences, 16th Edition, A. Oslo editor, Easton, Pennsylvania (1980).
Rolan et al., "The pharmacokinetics, tolerability and pharmacodynamics of tucaresol (589C80;4[2-formyl-3-hydroxyphenoxymethyl] benzoic acid), a potential anti-sickling agents, following oral adminstration to health subjects", Br. J. Clin. Pharmacol., 35(4):419-425 (1993).

(56) References Cited

OTHER PUBLICATIONS

Rooseboom et al., "Enzyme-catalyzed activation of anticancer prodrugs," Pharmacol. Rev. 56(1):53-102 (2004).
Ruchirawat et al., "A novel systhesis of apohoeadances," Tetrahedron Letters, 25(32):3485-3488 (1984).
Sahakitpichan et al., "A practical and highly efficient synthesis of lennoxamine and related isoindolobenzazepines," Tetrahedron, 60(19):4169-4172 (20040.
Sahm et al., "Synthesis of 2-arylbenzofurans," Justus Liebigs Annalen der Chemie, (4):522-38, includes English language abstract, (1974).
Sainsbury et al, "1,2-Dihydroisoquinolines, IV. Acylation," Tetrahedron, 22(8):2445-2452 (1966).
Sarodnick et al., "Quinoxalines XV. Convenient synthesis and structural study of pyrazolo [1,5-a]quinoxalines," Journal of Organic Chemistry, 74(3):1282-1287 (2009).
Silva et al., "Advances in proddrug design," Mini-Rev. Med. Chem., 5(10):893-914, 2005.
Singh et al., "Reductive-cyclization-mediated synthesis of fused polycyclic quinolines from Baylis-Hillman adducts of acrylonitrile: scope and limitations," European Journal of Organic Chemistry, (20):3454-3466 (2009).
Sobolov et al., "Effect of acyl chain length and branching on the enantioselectivity of *Candida rugosa* lipase in the kinetic resolution of 4-(2-difluoromethoxyphenyl)-substituted 1,4-dihydropyridine 3,5-diesters," J. Org. Chem., 67:401-410 (2002).
Srivastava et al., "Synthesis and biological evaluation of 4-substituted tetmzolo [4,5-a]quinolines and 2,3-disubstituted quinoline derivatives," Indian Journal of Chemistry, Section B: Organic Chemistry Including Medicinal Chemistry, 28B(7):562-573 (1989).
Starke et al., "Quinoxalines. Part 13: Synthesis and mass spectrometric study of aryloxymethylquinoxalines and benzo [b]furylquinoxalines," Tetrahedron, 60(29):6063-6078 (2004).
Swann et al., "Rates of reductive elimination of substituted nitrophenols from the (indol-3-yl)methyl position of indolequinones," Journal of the Chemical Society, Perkin Transactions 2, (8):1340-1345 (2001).
Testa et al., "Chapter 8, The hydrolysis in carboxylic Acid Ester Prodrugs," from Hydrolysis in Drug and Prodrug Metabolism: Chemistry, Biochemistry, and Enzymology, Wiley-VCH, Zurich, pp. 419-534, (2003).
Tome, A.C., "13.13, Product class 13: 1,2,3-triazoles," Science of Synthesis: Houben-Weyl Methods of Molecular Transformations, Georg Thieme Verlag publishers, Stuttgart, Germany, pp. 415-601, (2003).
Van Rompaey et al., "A versatile synthesis of 2-substituted 4-amino-1,2,4,5-tetrahydro-2-benzazepine-3-ones," Tetrahedron, 59(24):4421-4432 (2003).
Van Rompaey et al., "Synthesis and evaluation of the β-turn properties of 4-amino-1,2,4,5-tetrahydro-2-benzazepin-3-ones and of their spirocyclic derivative," European Journal of Organic Chemistry, (13):2899-2911 (2006).
Vicente et al., "Carbopalladation of maleate and fumarate esters and 1,1-dimethylallene with ortho-substituted aryl palladium complexes," Organometallics, 29(2):409-416 (2010).
Wang et al., "Studies of benzothiophene template as potent factor IXa (FIXa) inhibitors in thrombosis," Journal of Medicinal Chemistry, 53(4):1465-1472 (2010).
Warshawsky et al., "The synthesis of aminobenzazepinones as anti-phenylalanine dipeptide mimics and their use in NEP inhibition," Bioorganic & Medicinal Chemistry Letters, 6(8):957-962.
Yan et al., "Synthesis, crystal structure and antibacterial activity of di-n-butyltin carboxylate," Huaxue Tongbao, 70(4):313-316, includes English language abstract, (2007).
Yan et al., "Synthesis, crystal structure and antibacterial activity of di-n-butyltin di-2-(2-formylphenoxy)acetic ester," Yingyong Huaxue, 24(6):660-664, includes English language abstract, (2007).
Yoon et al., "The chirality conversion reagent for amino acids based on salicyl aldehyde," Bull. Korean Chem. Soc., 33(5):1715-18 (2012).
Zhang et al., "DFT study on $Ru^{II}$-catalyzed cyclization of terminal alkynals to cycloalkenes," International Journal of Quantum Chemistry, 109(4):679-687 (2009).
Zwaagstra et al., "Synthesis and structure-activity relationships of carboxylated chalcones: a novel series of Cys-LT1 (LTD4) Receptor Antagonists", Journal of Medicinal Chemistry, 40(7):1075-1089 (1997).
Behanna. Equity Research—Global Blood Therapeutics. Sep. 8, 2015. Retrieved from the Internet: URL:http://www.fintechsecurities.com/Websites/fintechsecurities/images/Research_Blog/Zacks/Sep2015/GBT150908.pdf.
International Search Report and Written Opinion dated Jan. 22, 2018 for PCT Application No. PCT/US2017/056352. 12 pages.
Kucera, et al. Evaluation of Ceolus(TM) microcrystalline cellulose grades for the direct compression of enteric-coated pellets. Drug Development and Industrial Pharmacy. Mar. 1, 2012; 38(3):341-350.
Mathur. "Microcrystalline Cellulose" In: "Handbook of Pharmaceutical Excipients, Second Edition", Jan. 1, 1994, The Pharmaceutical Press, London, pp. 84-87.
U.S. Appl. No. 61/581,053, filed Dec. 28, 2011, Metcalf et al.
U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.
Abdulmalik et al., Sickle cell disease: current therapeutic approaches, Expert Opinion Ther. Patents, 2005, vol. 15(11), pp. 1497-1506.
Abraham et al., Vanillin, a Potential Agent for the Treatment of Sickle Cell Anemia, Blood, Mar. 2005, vol. 77 (6), pp. 1334-1341.
Adhikary, P.K., et al., "A new antisickling agent: In vitro studies of its effect on S/S erythrocytes and on hemoglobin S", Experientia. 1978, vol. 34, No. 6, pp. 804-806.
Appendix A provided with Israel office action dated Aug. 11, 2016 for IL 233329.
Arya R, et al. "Tucaresol increases oxygen affinity and reduces haemolysis in subjects with sickle cell anaemia," Br. J. Haematol., 93(4):817-21 (1996).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Barnes, et al., "Prospects for new drugs for chronic obstructive pulmonary disease." The Lancet, 2004, 364, 985-996.
Barnes. "COPD: is there light at the end of the tunnel?" Current Opinion in Pharmacology, 2004, 4:263-272.
Beena et al., "Synthesis and antibacterial activity evaluation of metronidazole-triazole conjugates", Bioorganic & Medicinal Chemistry Letters, 2009, 19(5):1396-1398.
Bernstein. Crystals in Supramolecular Chemistry. ACA Transactions. 2004; 39:1-14.
Bernstein. Polymorphism in Molecular Crystals. Clarendon Press, Oxford. 2002. 115-118, 272.
Bonaventura, et al., "Molecular Controls of the Oxygenation and Redox Reactions of Hemoglobin." Antioxidants & Redox Signaling, 18(17), 2013, 2298-2313.
Bottino, et al. Study on the scope of tert-amino effect: new extensions of type 2 reactions to bridged biaryls. J. Phys. Org. Chem. 2012; 25(11):1033-1041.
Bradbury et al., "New nonpeptide angiotensin II receptor antagonists", Journal of Medicinal Chemistry, 1993, vol. 36, pp. 1245-1254.
Braga, et al. Making crystals from crystals: a green route to crystal engineering and polymorphism. Chem Commun (Camb). Aug. 7, 2005;(29):3635-45. Epub Jun. 15, 2005.
Caira. Crystalline Polymorphism of Organic Compounds. Topics in Current Chemistry, Springer, Berlin, DE. 1998; 198:163-208.
CAS Registry No. 1039841-20-7; entry dated Aug. 10, 2008.
CAS Registry No. 1096911-11-3; entry dated Jan. 28, 2009.

(56) References Cited

OTHER PUBLICATIONS

CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.
Chemical Abstract Registry No. 1142191-55-6, indexed in the Registry File on STN CA Online May 4, 2009.
Cheng, et al. Vilsmeier formylation of tert-anilines: dibenzo[b,f][1,5]diazocines and quinazolinium salts via the 1-amino effect'1. J. Chem. Soc., Perkin Trans 1. 1998; 1257-1262.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.
CMU Pharmaceutical polymorphism, internet p. 1-3 (2002) printout Apr. 3, 2008.
Concise Encyclopedia Chemistry, NY: Walter de Gruyter, 1993, 872-873.
Congreve et al. Application of Fragment Screening by X-ray Crystallography to the Discovery of Aminopyridines as Inhibitors of Beta-Secretase. J. Med. Chem. 50:1124-1132 (2007).
Cos et al., "Structure-Activity Relationship and Classification of Flavonoids as Inhibitors of Xanthine Oxidase and Superoxide Scavengers," J. Nat. Prod., (1998), 61:71-76.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN:1427163-92-5 & CN 102 952 062 A, Mar. 6, 2013, 2 pages.
Database Pubchem Compound Dec. 4, 2011 XP 003033770 (11 pages).
Database Registry, 2011, RN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Davidovich, et al. Detection of polymorphism by powder x-ray diffraction: interference by preferred orientation. Am. Pharm. Rev. 2004; 10, 12, 14, 16, 100.
Dean. Analytical Chemistry Handbook. University of Tennesse, Knoxville. McGraw-Hill, Inc. 1995; 10.24-10.26.
Deem. "Red Blood Cells and Hemoglobin in Hypoxic Pulmonary Vasoconstriction" Advances in experimental medicine and biology, (2006) 588, 217-231.
Desai et al. Preparation of N-[ro-(4-aryl-1-piperazinyl)ethyl/propyl]-3-hydroxyphthalimidines. Indian Journal of Chemistry. 39:455-457 (2000).
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).
Doelker, English translation of S.T.P, Pratiques (1999), 9(5), 399-409.
Doelker. English translation of Ann. Pharm. Fr., 2002, 60: 161-176.
Einfalt, et al. Methods of amorphization and investigation of the amorphous state. Acta Pharm. 2013; 63:305-334.
Epsztajn et al., "Application of organolithium", Tetrahedron, Elsevier Science Publishers, Amsterdam, NL, 1991, vol. 47, No. 9, pp. 1697-1706.
European Search Report and Search Opinion dated Aug. 4, 2015 for EP Application No. 12862525.8. 9 pages.
European Search Report and Search Opinion dated Jul. 21, 2016 for EP Application No. 14769616.5. 8 pages.
European Search Report and Search Opinion dated May 28, 2015 for EP Application No. 12862096.0. 13 pages.
European Search Report and Search Opinion dated Nov. 16, 2016 for EP Application No. 16194019.2. 13 pages.
European Search Report and Search Opinion dated Sep. 26, 2016 for EP Application No. 14768759.4. 6 pages.
Extended European Search Report and opinion dated Jul. 20, 2016 for EP Application No. 14768414.6. 10 pages.
Extended European Search Report and Search Opinion dated Jul. 18, 2016 for EP Application No. 14770695.6. 13 pages.
Extended European Search Report and Search Opinion dated Jul. 7, 2016 for EP Application No. 14768317.1. 7 pages.
Extended European Search Report and Search Opinion dated May 17, 2017 for EP Application No. 15746995.8. 8 pages.
Extended European Search Report and Search Opinion dated Nov. 23, 2015 for EP Application No. 12862525.8. 16 pages.
Gibson et al., "Novel small molecule bradykinin B2 receptor antagonists", Journal of Medicinal Chemistry, 2009, vol. 52, pp. 4370-4379.
Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.
Guillory (in Brittain ed.) Polymorphism in Pharmaceutical Solids. NY, Marcel Dekker, Inc. 1999; 1-2:183-226.
Hang, Song. "Pharmaceutical Separation Engineering" East China University of Technology Press. Aug. 31, 2011; 270-272. (in Chinese with English abstract).
He et al., "Prodrugs of Phosphonates, Phosphinates, and Phosphates", Prodrugs: Challenges and rewards Part 2, edited by Stella et al., 2007, pp. 223-264.
Heimbach et al., "Enzyme-mediated precipitation of patent drugs from their phosphate prodrugs", International Journal of Pharmaceutics, 261, p. 81-92, 2003.
Heimgartner et al., "Stereoselective synthesis of swainsonines from pyridines", Tetrahedron, Elsevier Science Publishers, Amsterdam, NL, 2005, vol. 61, No. 3, pp. 643-655.
Hoffman, et al. 3-Hydroxy-3-methyglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).
Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.
Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.
International Preliminary Report on Patentability for PCT/US2014/022846 dated Sep. 15, 2015. 7 pages.
International Preliminary Report on Patentability for PCT/US2014/022742 dated Sep. 15, 2015. 7 pages.
International Preliminary Report on Patentability for PCT/US2014/022733 dated Sep. 15, 2015. 11 pages.
International Preliminary Report on Patentability for PCT/US2014/022769 dated Sep. 15, 2015. 8 pages.
International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Aug. 4, 2017 for PCT Application No. PCT/US2017/032104. 10 pages.
International Search Report and Written Opinion dated Dec. 8, 2014 for PCT Application No. PCT/US2014/052575. 10 pages.
International Search Report and Written Opinion dated Jul. 22, 2014 for PCT Application No. PCT/US2014/022846. 11 pages.
International Search Report and Written Opinion dated Jul. 30, 2014 for PCT Application No. PCT/US2014/029682. 16 pages.
International Search Report and Written Opinion dated Jul. 31, 2014 for PCT Application No. PCT/US2014/022789. 13 pages.

(56) References Cited

OTHER PUBLICATIONS

International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 11, 2015 for PCT Application No. PCT/US2015/014589. 5 pages.
International Search Report and Written Opinion dated May 20, 2013 for PCT Application No. PCT/US2012/072183. 11 pages.
International Search Report and Written Opinion dated Nov. 28, 2014 for PCT Application No. PCT/US2014/052576. 10 pages.
International Search Report and Written Opinion dated Oct. 31, 2014 for PCT Application No. PCT/US2014/013575. 10 pages.
Israel office action dated Aug. 11, 2016 for Israeli Patent Application No. 233329.
Ito et al., A medium-term rat liver bioassay for rapid in vivo detection of carcinogenic potential of chemicals,01 D Cancer Science, Jan. 2003, 94, pp. 3-8.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Keidan, et al. Effect of BW12C on oxygen affinity of hemoglobin in sickle-cell disease. The Lancet. 1986; 327(8485):831-834.
Kirk-Othmer Encyclopedia of Chemical Technology. 2002; 8:95-147.
Klis, et al. Halogen-lithium exchange versus deprotonation: synthesis of diboronic acids derived from aryl-benzyl ethers. Tetrahedron Letters, 48(7):1169-1173 (2007).
Kratochvil. Chapter 8 Solid Forms of Pharmaceutical Molecules. J. Sestak et al. (eds.), Glassy, Amorphous and Nano-Crystalline Materials. Hot Topics in Thermal Analysis and Calorimetry 8, 2011, pp. 129-140.
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Luan, et al. TOPS-MODE model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, Il Farmaco, 1996, vol . 51, No. 8, 9, pp. 579-587.
Marchetti et al., "Synthesis and biological evaluation of 5-substituted O4-alkylpyrimidines as CDK2 inhibitors," Org. Biomol. Chem, 2010, vol. 8, pp. 2397-2407.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
Mesguiche et al., "4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.
Metcalf, et al., "Discovery of GBT440, an Orally Bioavailable R-State Stabilizer of Sickle Cell Hemoglobin," ACS Med. Chem. Lett., 2017, 8, 321-326.
Muzaffar, et al., "Polymorphism and Drug Availability: a Review"J of Pharm. (Lahore), 1979, 1(1), 59-66.
Notice of Allowance dated Dec. 19, 2014 for U.S. Appl. No. 13/730,730. 11 pages.
OECD SIDS "SIDS Initial Assessment Report for 13th SIAM," Nov. 2001, pp. 1-95.
Office Action dated Aug. 29, 2014 for U.S. Appl. No. 13/730,730. 17 pages.

Office Action dated Dec. 3, 2013 for U.S. Appl. No. 13/730,674. 8 pages.
Office Action dated Jul. 6, 2015 for U.S. Appl. No. 13/815,874. 14 pages.
Office Action dated Jun. 12, 2015 for CN Application No. 201280070743.5. 13 pages.
Office Action dated Jun. 29, 2015 for U.S. Appl. No. 13/815,810. 19 pages.
Office Action dated Jun. 30, 2014 for U.S. Appl. No. 13/730,674. 9 pages.
Office Action dated Sep. 18, 2013 for U.S. Appl. No. 13/730,674. 10 pages.
Oh, et al. Solid-phase synthesis of 1,3-oxazolidine derivatives. Tetrahedron Letters. 2000; 41:5069-5072.
Otsuka, et al., "Effect of Polymorphic Forms of Bulk Powders on Pharmaceutical Properties of Carbamazepine Granules." Chem. Pharm. Bull., 47(6) 852-856 (1999).
Patani, et al. Bioisosterism: A Rational Approach in Drug Design. J. Chem Rev. 1996, 96(8), pp. 3147-3176.
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Prohens, et al. Polymorphism in pharmaceutical industry. The Pharmacist. Apr. 1, 2007; 373:58-68. (in Spanish with English abstract).
Rodriguez-Spong, et al. General principles of pharmaceutical solid polymorphism: a supramolecular perspective. Adv Drug Deliv Rev. Feb. 23, 2004;56(3):241-74.
Safo, et al. Structural basis for the potent antisickling effect of a novel class of five-membered heterocyclic aldehydic compounds. J Med Chem. Sep. 9, 2004;47(19):4665-76.
Schudel, et al. Uber die Chemie des Vitamins E. Helvetica Chimica Acta. 1963; 66:636-649.
Seddon. Pseudopolymorph: A Polemic. The QUILL Centre, The Queen's University of Belfast, United Kingdom. Jul. 26, 2004. 2 pages.
Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Siddiqui et al., "The Presence of Substitutents on the Aryl Moiety of the Aryl Phosphoramidate Derivative of d4T Enhances Anti-HIV Efficacy in Cell Culture-Activity Relationship," J. Med. Chem., (1999), 42:393-399.
Singhal, et al., "Drug Polymorphism and Dosage Form Design: a Practical Perspective" Advanced Drug Delivery reviews 56, p. 335-347 (2004).
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley. Solubilizing excipients in oral and injectable formulations. Pharm Res. Feb. 2004;21(2):201-30.
Table of Compounds, each of which can be found either in Table 1 of U.S. Pat. No. 9,018,210 or Table 1 of U.S. Pat. No. 9,012,450.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
Tsuge, et al. Suppressive Effect of Vitamin B6-Sugar Derivatives on the Proliferation of Feline Mammary Tumor Cell, FRM. Vitamins (Japan), 2006; 80(11):537-542. (in Japanese with English Abstract).
U.S. Pharmacopia #23, National Formulary #18, 1995, 1843-1844.
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
Vichinsky. "Emerging 'A' therapies in hemoglobinopathies: agonists, antagonists, antioxidants, and arginine." Hematology 2012, 271-275.

(56) References Cited

OTHER PUBLICATIONS

Vippagunta, et al. Crystalline Solids. Advanced Drug Delivery Reviews. 2001; 48:3-26.

Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.

Yang, et al. Structural requirement of chalcones for the inhibitory activity of interleukin-5. Bioorg Med Chem. Jan. 1, 2007;15(1):104-11. Epub Oct. 10, 2006.

Zhang, et al. A selective fluorescent chemosensor with 1, 2, 4-triazole as subunit for Cu (II) and its application in imaging Cu (II) in living cells. Dyes and Pigments. 2012; 92(3):1370-1375.

Zhang, et al. Current prodrug strategies for improving oral absorption of nucleoside analogues. Asian Journal of Pharmaceutical Sciences. Apr. 2014; 9(2):65-74.

Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.

\* cited by examiner

COMPOUNDS AND USES THEREOF FOR THE MODULATION OF HEMOGLOBIN

CROSS-REFERENCE TO RELATED APPLICATIONS

This application is the U.S. 371 national stage application of International Patent Application No. PCT/US2014/022736 entitled "COMPOUNDS AND USES THEREOF FOR THE MODULATION OF HEMOGLOBIN" filed on Mar. 10, 2014; which claims the benefit of U.S. Provisional Application No. 61/905,802 entitled "COMPOUNDS AND USES THEREOF FOR THE MODULATION OF HEMOGLOBIN" filed on Nov. 18, 2013; and is a continuation-in-part of U.S. patent application Ser. No. 13/815,874 entitled "COMPOUNDS AND USES THEREOF FOR THE MODULATION OF HEMOGLOBIN" filed on Mar. 15, 2013, now U.S. Pat. No. 9,604,999, the disclosures of which are incorporated herein by reference in their entirety and for all purposes.

FIELD OF THE INVENTION

This invention provides compounds and pharmaceutical compositions suitable as allosteric modulators of hemoglobin, methods and intermediates for their preparation, and methods for their use in treating disorders mediated by hemoglobin and disorders that would benefit from tissue and/or cellular oxygenation.

STATE OF THE ART

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin (Hb).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, allowing HbS to become susceptible to polymerization to give the HbS containing red blood cells their characteristic sickle shape. The sickled cells are also more rigid than normal red blood cells, and their lack of flexibility can lead to blockage of blood vessels. U.S. Pat. No. 7,160,910 discloses compounds that are allosteric modulators of hemoglobin. However, a need exists for additional therapeutics that can treat disorders that are mediated by Hb or by abnormal Hb such as HbS.

SUMMARY OF THE INVENTION

This invention relates generally to compounds and pharmaceutical compositions suitable as allosteric modulators of hemoglobin. In some aspects, this invention relates to methods for treating disorders mediated by hemoglobin and disorders that would benefit from tissue and/or cellular oxygenation.

In certain aspects of the invention, a compound of formula (I) is provided:

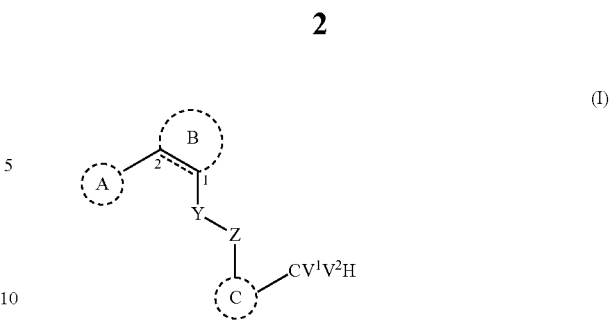

or a tautomer thereof, or a pharmaceutically acceptable salt of each thereof, wherein ring A is an optionally substituted 4-10 membered cycloalkyl or 4-10 membered heterocycle containing up to 5 ring heteroatoms, wherein the heteroatom is selected from the group consisting of O, N, S, and oxidized forms of N and S;

ring B is a $C_6$-$C_{10}$aryl or 5-10 membered heteroaryl having 1-3 nitrogen atoms, preferably 1-2 nitrogen atoms and more preferably 1 nitrogen atom, or oxidized versions thereof, wherein the aryl or heteroaryl is optionally substituted;

⚡ is a single or a double bond;

each Y and Z is independently $CR^{10}R^{11}$, O, S, SO, $SO_2$, or $NR^{12}$; each $R^{10}$ and $R^{11}$ independently is hydrogen or $C_1$-$C_3$ alkyl optionally substituted with halo, OH, or $C_1$-$C_6$ alkoxy, or $CR^{10}R^{11}$ is C=O; $R^{12}$ is hydrogen or $C_1$-$C_6$ alkyl; provided that if one of Y and Z is O, S, SO, $SO_2$, then the other is not CO, and provided that Y and Z are both not heteroatoms or oxidized forms thereof;

ring C is $C_6$-$C_{10}$ aryl, optionally substituted;

$V^1$ and $V^2$ independently are $C_1$-$C_6$ alkoxy; or $V^1$ and $V^2$ together with the carbon atom they are attached to form a ring of formula:

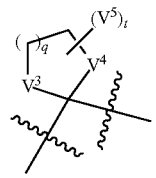

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl; and $R^{84}$ is optionally substituted $C_1$-$C_6$ alkyl.

In certain aspects of the invention, a compound of formula (IA) is provided:

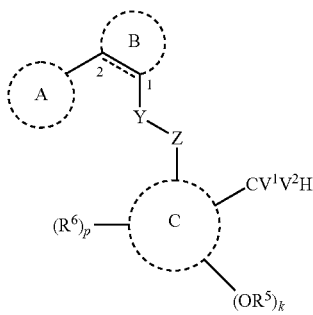

(IA)

wherein $R^5$ is hydrogen, $C_1$-$C_6$ alkyl or a prodrug moiety R, wherein the $C_1$-$C_6$ alkyl is optionally substituted with 1-5 halo;

$R^6$ is halo, $C_1$-$C_6$ alkyl, $C_1$-$C_6$ alkoxy, $C_1$-$C_6$ alkylthio, $C_1$-$C_6$ S(O)—, $C_1$-$C_6$ S(O)$_2$—, wherein the $C_1$-$C_6$ alkyl is optionally substituted with 1-5 halo; or $R^6$ is 4-10 membered cycloalkyl or heterocycle substituted with an R'R'N-moiety wherein each R' is independently $C_1$-$C_6$ alkyl or hydrogen;

k is 0 or 1;

p is 0, 1, 2 or 3;

and the remaining variables are defined as above.

In further aspects of the invention, a composition is provided comprising any of the compounds described herein, and at least a pharmaceutically acceptable excipient.

In still further aspects of the invention, a method is provided for increasing oxygen affinity of hemoglobin S in a subject, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

DETAILED DESCRIPTION OF THE INVENTION

Definitions

It must be noted that as used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, $C_m$-$C_n$, such as $C_1$-$C_{12}$, $C_1$-$C_8$, or $C_1$-$C_6$ when used before a group refers to that group containing m to n carbon atoms.

The term "alkoxy" refers to —O-alkyl. The term alkylthio is —S-alkyl.

The term "alkyl" refers to monovalent saturated aliphatic hydrocarbyl groups having from 1 to 30 carbon atoms (i.e., $C_1$-$C_{30}$ alkyl) or 1 to 22 carbon atoms (i.e., $C_1$-$C_{22}$ alkyl), 1 to 8 carbon atoms (i.e., $C_1$-$C_8$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3$)($CH_3CH_2$)CH—), t-butyl (($CH_3)_3C$—), n-pentyl ($CH_3CH_2CH_2CH_2CH_2$—), and neopentyl (($CH_3)_3CCH_2$—).

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

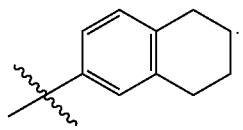 [SMILES: *c1ccc2c(c1)CCCC2]

The term "—$CO_2H$ ester" refers to an ester formed between the —$CO_2H$ group and an alcohol, preferably an aliphatic alcohol. A preferred example included —$CO_2R^E$, wherein $R^E$ is alkyl or aryl group optionally substituted with an amino group.

The term "chiral moiety" refers to a moiety that is chiral. Such a moiety can possess one or more asymmetric centers. Preferably, the chiral moiety is enantiomerically enriched, and more preferably a single enantiomer. Non limiting examples of chiral moieties include chiral carboxylic acids, chiral amines, chiral amino acids, such as the naturally occurring amino acids, chiral alcohols including chiral steroids, and the likes.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamentyl, and the like. The condensed rings may or may not be non-aromatic hydrocarbyl rings provided that the point of attachment is at a cycloalkyl carbon atom. For example, and without limitation, the following is a cycloalkyl group:

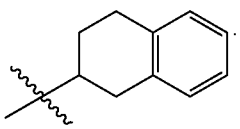 [SMILES: *C1CCc2ccccc2C1]

The term "halo" refers to F, Cl, Br, and/or I.

The term "heteroaryl" refers to a monovalent, aromatic mono-, bi-, or tricyclic ring having 2-16 ring carbon atoms and 1-8 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

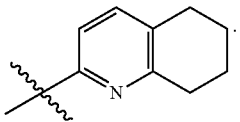 [SMILES: *c1ccc2c(n1)CCCC2]

The term "heterocyclyl" or heterocycle refers to a non-aromatic, mono-, bi-, or tricyclic ring containing 2-12 ring carbon atoms and 1-8 ring heteroatoms selected preferably from N, O, S, and P and oxidized forms of N, S, and P, provided that the ring contains at least 3 ring atoms. While heterocyclyl preferably refers to saturated ring systems, it also includes ring systems containing 1-3 double bonds, provided that the ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

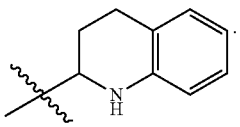 [SMILES: *C1CCc2ccccc2N1]

The term "hydrolyzing" refers to breaking an $R^H$—O—CO—, $R^H$—O—CS—, or an $R^H$—O—SO$_2$-moiety to an $R^H$—OH, preferably by adding water across the broken bond. A hydrolyzing is performed using various methods well known to the skilled artisan, non limiting examples of which include acidic and basic hydrolysis.

The term "oxo" refers to a C=O group, and to a substitution of 2 geminal hydrogen atoms with a C=O group.

The term "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, NO$_2$, —N$_2$+, —CO$_2$R$^{100}$, —OR$^{100}$, —SR$^{100}$, —SOR$^{100}$, —SO$_2$R$^{100}$, —NR$^{101}$R$^{102}$, —CONR$^{101}$R$^{102}$, —SO$_2$NR$^{101}$R$^{102}$, C$_1$-C$_6$ alkyl, C$_1$-C$_6$ alkoxy, —CR$^{100}$=C(R$^{100}$)$_2$, —CCR$^{100}$, C$_3$-C$_{10}$ cycloalkyl, C$_3$-C$_{10}$ heterocyclyl, C$_6$-C$_{12}$ aryl and C$_2$-C$_{12}$ heteroaryl, wherein each R$^{100}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each alkyl, cycloalkyl, heterocyclyl, aryl, or heteroaryl is optionally substituted with 1-3 halo, 1-3 C$_1$-C$_6$ alkyl, 1-3 C$_1$-C$_6$ haloalkyl or 1-3 C$_1$-C$_6$ alkoxy groups. Preferably, the substituents are selected from the group consisting of chloro, fluoro, —OCH$_3$, methyl, ethyl, iso-propyl, cyclopropyl, vinyl, ethynyl, —CO$_2$H, —CO$_2$CH$_3$, —OCF$_3$, —CF$_3$ and —OCHF$_2$.

R$^{101}$ and R$^{102}$ independently is hydrogen; C$_1$-C$_8$ alkyl, optionally substituted with —CO$_2$H or an ester thereof, C$_1$-C$_6$ alkoxy, oxo, —CR$^{103}$=C(R$^{103}$)$_2$, —CCR, C$_3$-C$_{10}$ cycloalkyl, C$_3$-C$_{10}$ heterocyclyl, C$_6$-C$_{12}$ aryl, or C$_2$-C$_{12}$ heteroaryl, wherein each R$^{103}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each cycloalkyl, heterocyclyl, aryl, or heteroaryl is optionally substituted with 1-3 alkyl groups or 1-3 halo groups, or R$^{101}$ and R$^{102}$ together with the nitrogen atom they are attached to form a 5-7 membered heterocycle.

The term "pharmaceutically acceptable" refers to safe and non-toxic for in vivo, preferably, human administration.

The term "pharmaceutically acceptable salt" refers to a salt that is pharmaceutically acceptable.

The term "salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, NH$_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisalfate, mono-, di-, and tribasic phosphate, mesylate, tosylate, and the likes.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example in a subject at risk of suffering from such a disease or disorder, thereby substantially averting onset of the disease or disorder.

The term "effective amount" refers to an amount that is effective for the treatment of a condition or disorder by an intranasal administration of a compound or composition described herein. In some embodiments, an effective amount of any of the compositions or dosage forms described herein is the amount used to treat a disorder mediated by hemoglobin or a disorder that would benefit from tissue and/or cellular oxygenation of any of the compositions or dosage forms described herein to a subject in need thereof.

The term "carrier" as used herein, refers to relatively nontoxic chemical compounds or agents that facilitate the incorporation of a compound into cells, e.g., red blood cells, or tissues.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity. For example, see the reference Nogrady, 1985, Medicinal Chemistry A Biochemical Approach, Oxford University Press, New York, pages 388-392. Prodrugs can also be prepared using compounds that are not drugs.

Compounds

In certain aspects of the invention, a compound of formula (I) is provided:

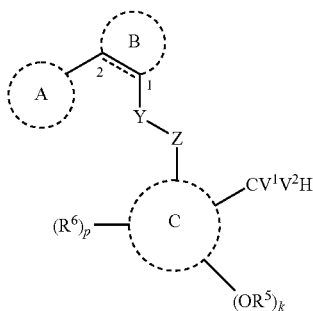

(I)

or a tautomer thereof, or a pharmaceutically acceptable salt of each thereof, wherein ring A is an optionally substituted 4-10 membered cycloalkyl or 4-10 membered heterocycle containing up to 5 ring heteroatoms, wherein the heteroatom is selected from the group consisting of O, N, S, and oxidized forms of N and S;

ring B is a $C_6$-$C_{10}$ aryl or 5-10 membered heteroaryl having 1-3 nitrogen atoms, preferably 1-2 nitrogen atoms and more preferably 1 nitrogen atom, or oxidized versions thereof, wherein the aryl or heteroaryl is optionally substituted;

⚊⚋ is a single or a double bond;

each Y and Z is independently $CR^{10}R^{11}$, O, S, SO, $SO_2$, or $NR^{12}$; each $R^{10}$ and $R^{11}$ independently is hydrogen or $C_1$-$C_3$ alkyl optionally substituted with halo, OH, or $C_1$-$C_6$ alkoxy, or $CR^{10}R^{11}$ is C=O; $R^{12}$ is hydrogen or $C_1$-$C_6$ alkyl; provided that if one of Y and Z is O, S, SO, $SO_2$, then the other is not CO, and provided that Y and Z are both not heteroatoms or oxidized forms thereof;

ring C is $C_6$-$C_{10}$ aryl;

$V^1$ and $V^2$ independently are $C_1$-$C_6$ alkoxy; or $V^1$ and $V^2$ together with the carbon atom they are attached to form a ring of formula:

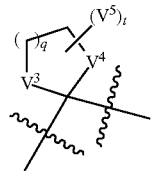

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^5$ is hydrogen, $C_1$-$C_6$ alkyl or a prodrug moiety R, wherein the $C_1$-$C_6$ alkyl is optionally substituted with 1-5 halo;

$R^6$ is halo, $C_1$-$C_6$ alkyl, $C_1$-$C_6$ alkoxy, $C_1$-$C_6$ alkylthio, $C_1$-$C_6$ S(O)—, $C_1$-$C_6$ S(O)$_2$—, wherein the $C_1$-$C_6$ alkyl is optionally substituted with 1-5 halo; or $R^6$ is 4-10 membered cycloalkyl or heterocycle substituted with an R'R'N-moiety wherein each R' is independently $C_1$-$C_6$ alkyl or hydrogen;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl;

$R^{84}$ is optionally substituted $C_1$-$C_6$ alkyl;

k is 0 or 1; and p is 0, 1, 2 or 3.

In certain embodiments, t is 0. In certain embodiments, t is 1. In certain embodiments, t is 2. In certain embodiments, t is 3.

Preferably, in certain embodiments, Y and Z are both not a heteroatom or a heteroatom containing moiety. Preferably, one of Y and Z is a methylene or substituted methylene and the other is a heteroatom or a heteroatom containing moiety. More preferably, Y is an alkylene, and Z is a heteroatom or a heteroatom containing moiety, which, yet more preferably is oxygen.

Preferably, $V^1$ and $V^2$ together with the carbon atom they are attached to form a ring of formula:

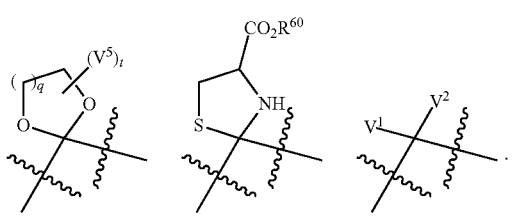

In some embodiments, $V^1$ and $V^2$ independently are $C_1$-$C_6$ alkoxy; or $V^1$ and $V^2$ together with the carbon atom they are attached to form a ring of formula:

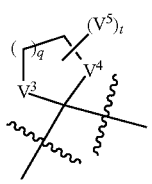

wherein each $V^3$ and $V^4$ are independently O, S, or NH, provided that when one of $V^3$ and $V^4$ is S the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, and wherein the remaining variables are defined herein.

In certain aspects of the invention, the compound of Formula (I) is of Formula (II):

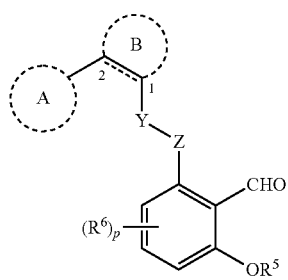

(II)

wherein the remaining variables are defined herein.

In certain aspects of the invention, the compound of Formula (I) is of Formula (IIA):

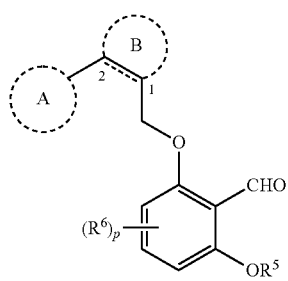

(II)

wherein
the variables are defined herein.

In some embodiments, ring A is optionally substituted with 1-3: halo, $C_1$-$C_6$ alkyl, $COR^{15}$ and/or $COOR^{15}$; wherein $R^{15}$ is optionally substituted $C_1$-$C_6$ alkyl, optionally substituted $C_6$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S.

In some embodiments, ring B is optionally substituted with 1-3: halo, $C_1$-$C_6$ alkyl $COR^{15}$ and/or $COOR^{15}$; wherein $R^{15}$ is optionally substituted $C_1$-$C_6$ alkyl, optionally substituted $C_6$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S.

In some embodiments, the compound is selected from the group consisting of

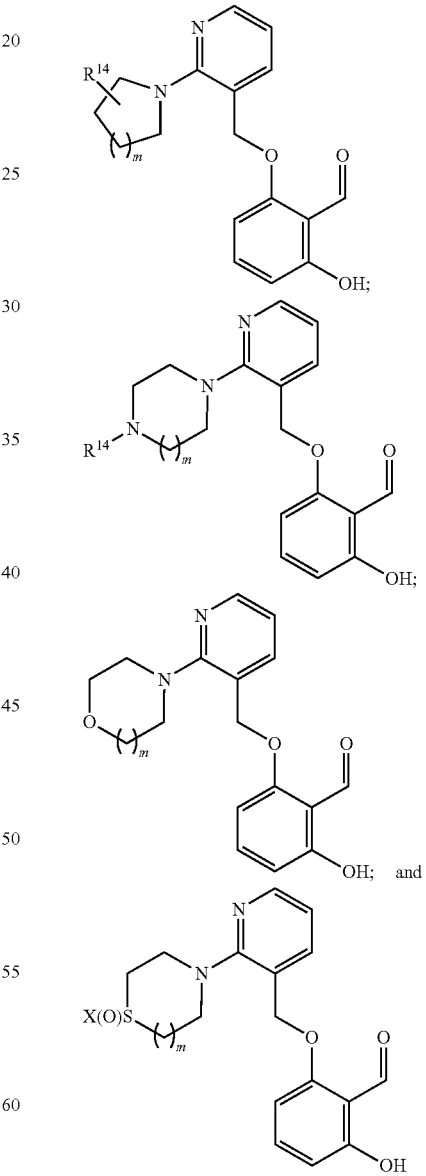

or an N oxide thereof, wherein
$R^{14}$ is $C_1$-$C_6$ alkyl, $C_3$-$C_8$ cycloalkyl, $COR^{15}$ or $COOR^{15}$;
$R^{15}$ is optionally substituted $C_1$-$C_6$ alkyl, optionally substituted $C_6$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S;

x is 0, 1, or 2;
p is 0, 1, and 2; and
m is 0, 1 or 2.

In one embodiment, the compound is

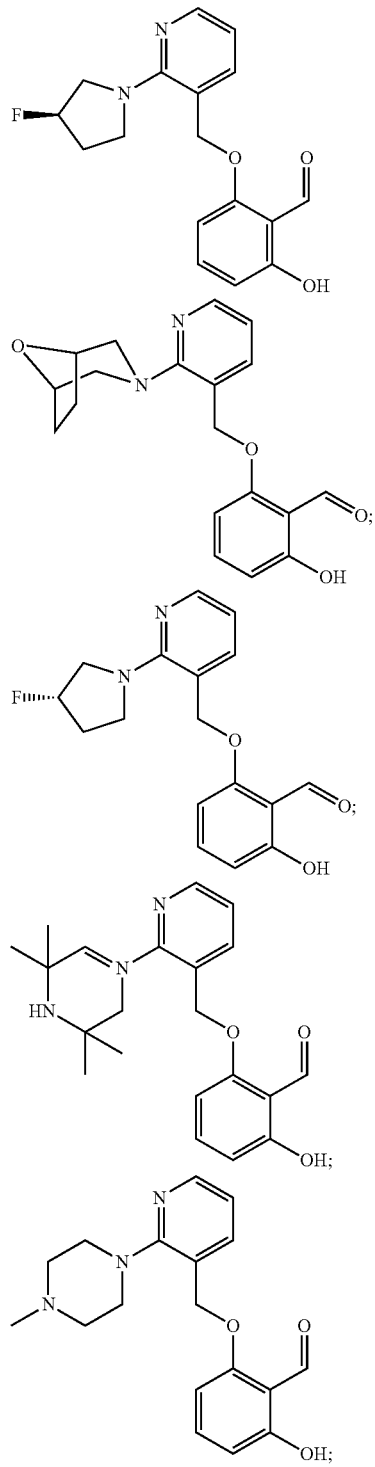

-continued

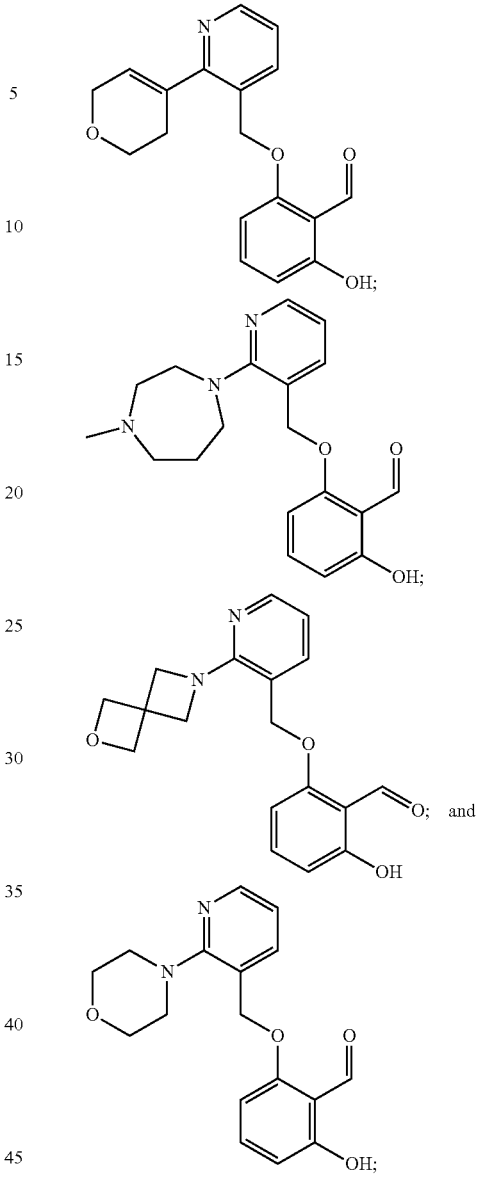

or a prodrug thereof, or a pharmaceutically acceptable salt of each thereof.

Other compounds provided herein are included in the Examples section.

Prodrug Moiety

In one aspect, R is hydrogen, a phosphate or a diphosphate containing moiety, or another promoiety or prodrug moiety. Preferably the prodrug moiety imparts at least a 2 fold, more preferably a 4 fold, enhanced solubility and/or bioavailability to the active moiety (where R is hydrogen), and more preferably is hydrolyzed in vivo. The promoieties are structurally and functionally defined herein.

In one embodiments, R is —$COR^{90}$, $CO_2R^{91}$, or $CONR^{92}R^{93}$ wherein $R^{90}$ and $R^{91}$ independently are $C_1$-$C_6$ alkyl, $C_3$-$C_8$ cycloalkyl, 4-9 membered heterocycle, or a 5-10 membered heteroaryl, each containing at least 1 basic nitrogen moiety; and $R^{92}$ and $R^{93}$ independently are $C_1$-$C_6$ alkyl; $C_3$-$C_8$ cycloalkyl, 4-9 membered heterocycle, or a 5-10 membered heteroaryl, each containing at least 1 basic nitrogen moiety; or $R^{92}$ and $R^{93}$ together with the nitrogen atom they are bonded to for a 4-9 member heterocycle substituted with at least 1 amino, $C_1$-$C_6$ alkyl amino, or di $C_1$-$C_6$ alkylamino group.

In certain embodiments, R is —C(O)$R^{31}$, C(O)O$R^{31}$, or CON($R^{13}$)$_2$;

each $R^{31}$ is independently a $C_1$-$C_6$ alkyl; $C_3$-$C_8$ cycloalkyl, 4-9 membered heterocycle, or a 5-10 membered heteroaryl, containing at least 1 basic nitrogen moiety; and each $R^{13}$ independently are $C_1$-$C_6$ alkyl; $C_3$-$C_8$ cycloalkyl, 4-9 membered heterocycle, or a 5-10 membered heteroaryl, containing at least 1 basic nitrogen moiety; or 2 $R^{13}$ together with the nitrogen atom they are bonded to for a 4-9 member heterocycle substituted with at least 1 amino, $C_1$-$C_6$ alkyl amino, or di $C_1$-$C_6$ alkylamino group.

In one aspect, R is C(O)O$R^{31}$, C(S)O$R^{31}$, C(O)S$R^{31}$ or CO$R^{31}$, wherein $R^{31}$ is as defined herein.

In one embodiment, $R^{31}$ is a group of the formula $(CR^{32}R^{33})_eNR^{34}R^{35}$, wherein each $R^{32}$ and $R^{33}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl or $R^{32}$ and $R^{33}$ together with the carbon atom they are bond to form a $C_3$-$C_8$ cycloalkyl, $C_6$-$C_{10}$ aryl, $C_3$-$C_9$ heterocyclyl or $C_3$-$C_9$ heteroaryl ring system, or 2 adjacent $R^{32}$ moieties or 2 adjacent $R^{33}$ moieties together with the carbon atom they are bond to form a $C_3$-$C_8$ cycloalkyl, $C_6$-$C_{10}$ aryl, $C_3$-$C_9$ heterocyclyl or $C_3$-$C_9$ heteroaryl ring system;

each $R^{34}$ and $R^{35}$ is a $C_1$-$C_8$ alkyl, $C_3$-$C_9$ heterocyclyl, $C_3$-$C_8$ cycloalkyl, or $R^{34}$ and $R^{35}$ together with the nitrogen atom they are bond to form a $C_3$-$C_8$ cycloalkyl or $C_3$-$C_9$ heterocyclyl ring system;

each heterocyclic and heteroaryl ring system is optionally substituted with $C_1$-$C_3$ alkyl, —OH, amino and carboxyl groups; and e is an integer of from 1 to 4.

In some less preferred embodiments $R^{34}$ and $R^{35}$ can be hydrogen.

In one embodiment, the subscript e is preferably 2 and each $R^{32}$ and $R^{33}$ is preferably independently selected from the group, H, $CH_3$, and a member in which $R^{32}$ and $R^{33}$ are joined together to form a cyclopropyl, cyclobutyl, cyclopentyl, cyclohexyl, or 1,1-dioxo-hexahydro-1$\Delta^6$-thiopyran-4-yl or tetrahydropyran-4-yl group.

With regard to the prodrug group, preferred embodiments are compounds wherein $NR^{34}R_{35}$ is morpholino.

In one embodiment, R is:

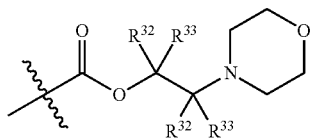

wherein each $R^{32}$ and $R^{33}$ is independently H, $C_1$-$C_8$ alkyl, or optionally, if both present on the same substituent, may be joined together to form a $C_3$-$C_8$ cycloalkyl, $C_6$-$C_{10}$ aryl, $C_3$-$C_9$ heterocyclyl or $C_3$-$C_9$ heteroaryl ring system.

Within this embodiment, each $R^{32}$ and $R^{33}$ is independently, H, $CH_3$, or are joined together to form a cyclopropyl, cyclopbutyl, cyclopentyl, cyclohexyl, 1,1-dioxo-hexahydro-1$\lambda^6$-thiopyran-4-yl or tetra hydropyran-4-yl group.

In a preferred embodiment, linkage of the prodrug moiety to the rest of the active molecule is stable enough so that the serum half life of the prodrug is from about 8 to about 24 hours.

In an embodiment of the invention, the prodrug moiety comprises a tertiary amine having a pKa near the physiological pH of 7.5. Any amines having a pKa within 1 unit of 7.5 are suitable alternatives amines for this purpose. The amine may be provided by the amine of a morpholino group. This pKa range of 6.5 to 8.5 allows for significant concentrations of the basic neutral amine to be present in the mildly alkaline small intestine. The basic, neutral form of the amine prodrug is lipophilic and is absorbed through the wall of the small intestine into the blood. Following absorption into the bloodstream, the prodrug moiety is cleaved by esterases which are naturally present in the serum to release an active compound.

Examples of R include, without limitation:

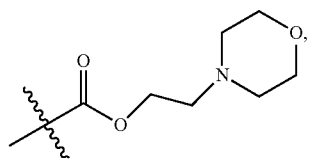

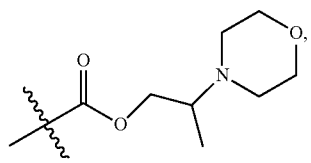

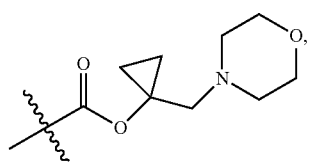

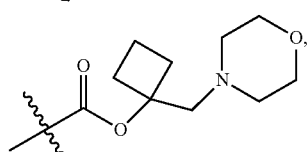

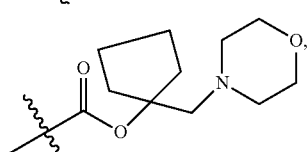

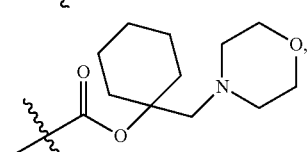

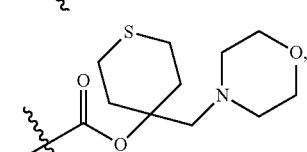

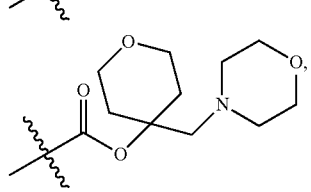

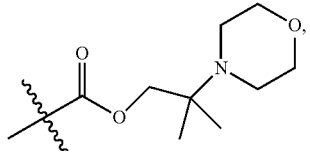

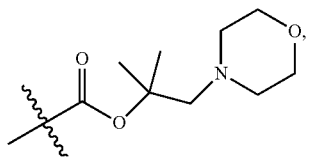

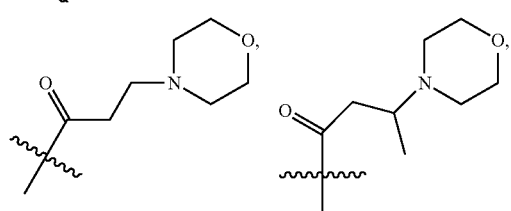

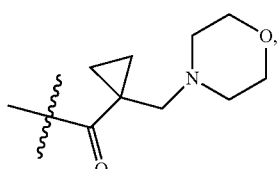

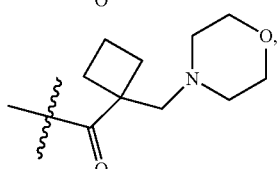

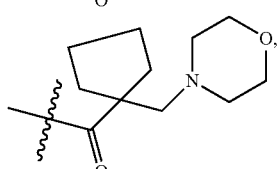

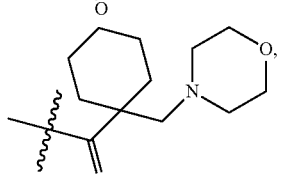

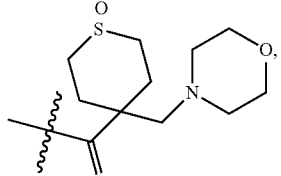

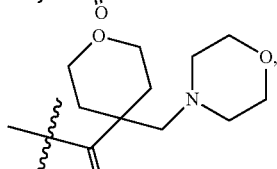

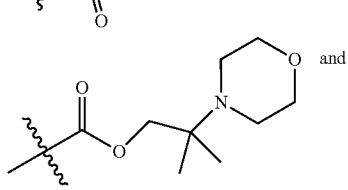 and

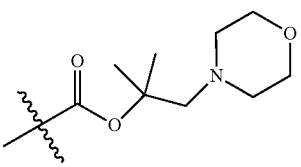

In another embodiment, R is as tabulated below:

| R | m | R³⁴ | R³⁵ | NR³⁴R³⁵ |
|---|---|-----|-----|---------|
| C(O)O(CH₂)ₘNR³⁴R³⁵ | 1 | Me | Me | |
| C(O)O(CH₂)ₘNR³⁴R³⁵ | 2 | Me | Me | |
| C(O)O(CH₂)ₘNR³⁴R³⁵ | 3 | Me | Me | |
| C(O)O(CH₂)ₘNR³⁴R³⁵ | 4 | Me | Me | |
| C(O)O(CH₂)ₘNR³⁴R³⁵ | 1 | | | morpholine |
| C(O)O(CH₂)ₘNR³⁴R³⁵ | 2 | | | morpholine |
| C(O)O(CH₂)ₘNR³⁴R³⁵ | 3 | | | morpholine |
| C(O)O(CH₂)ₘNR³⁴R³⁵ | 4 | | | morpholine |
| C(O)O(CH₂)ₘNR³⁴R³⁵ | 2 | Me | Me | |
| C(O)O(CH₂)ₘNR³⁴R³⁵ | 3 | Me | Me | |
| C(O)O(CH₂)ₘNR³⁴R³⁵ | 4 | Me | Me | |
| C(O)O(CH₂)ₘNR³⁴R³⁵ | 2 | | | morpholine |
| C(O)O(CH₂)ₘNR³⁴R³⁵ | 3 | | | morpholine |
| C(O)O(CH₂)ₘNR³⁴R³⁵ | 4 | | | morpholine |
| P(O)(OH)₂ | | | | | an N oxide thereof, or a pharmaceutically acceptable salt of each thereof.

In another aspect, R is,

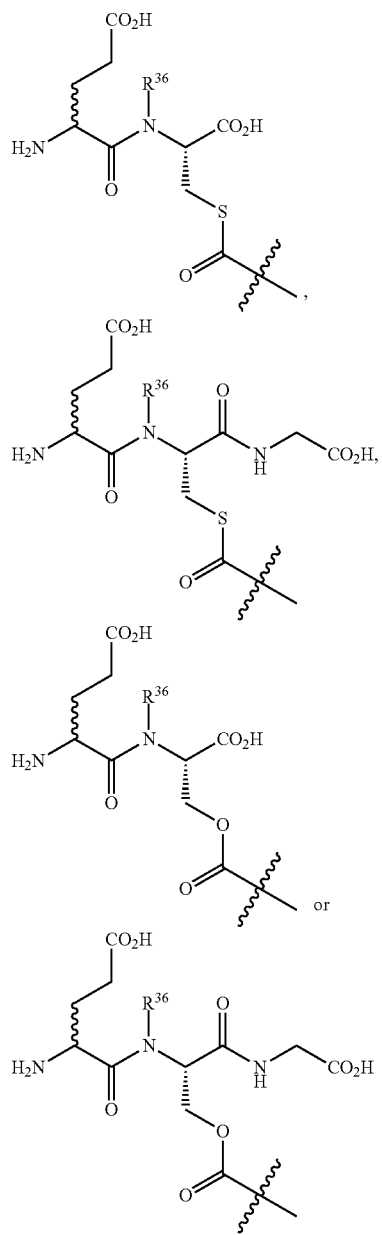

wherein
$R^{36}$ is lower alkyl (e.g. $C_1$-$C_6$ alkyl).
In yet another aspect, R is:

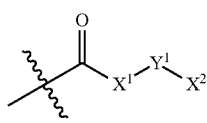

wherein $X^1$, $Y^1$ and $X^2$ are as defined herein.

In one embodiment, $X^1$ is selected from the group consisting of O, S and $NR^{37}$ wherein $R^{37}$ is hydrogen or $C_1$-$C_6$ alkyl;

$Y^1$ is —$C(R^{38})_2$— or a sugar moiety, wherein each $R^{38}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl;

$X^2$ is selected from the group consisting of halogen, $C_1$-$C_6$ alkoxy, diacylglycerol, amino, $C_1$-$C_6$ alkylamino, $C_1$-$C_6$ dialkylamino, $C_1$-$C_6$ alkylthio, a PEG moiety, a bile acid moiety, a sugar moiety, an amino acid moiety, a di- or tri-peptide, a PEG carboxylic acid, and —U—V wherein
U is O or S; and
V is selected from the group consisting of $C_1$-$C_6$ alkyl, $C_3$-$C_8$ cycloalkyl, $C_3$-$C_9$ heterocyclyl, $C_6$-$C_{10}$ aryl, $C_3$-$C_9$ heteroaryl, $C(W^2)X^3$, $PO(X^3)_2$, and $SO_2X^3$;
wherein $W^2$ is O or $NR^{39}$
wherein $R^{39}$ is hydrogen or $C_1$-$C_6$ alkyl, $C_3$-$C_8$ cycloalkyl, $C_3$-$C_9$ hetrocyclyl, $C_6$-$C_{10}$ aryl, or $C_3$-$C_9$ heteroaryl; and
each $X^3$ is independently amino, hydroxyl, mercapto, $C_1$-$C_6$ alkyl, heteroalkyl, cycloalkyl, hetrocyclyl, aryl, or heteroaryl, $C_1$-$C_6$ alkoxy, $C_1$-$C_6$ alkylamino, $C_1$-$C_6$ dialkylamino, $C_1$-$C_6$ alkylthio, a bile acid based alkoxy group, a sugar moiety, a PEG moiety, and) —O—$CH_2$—$CH(OR^{40})$$CH_2X^4R^{40}$,
wherein:
$X^4$ is selected from the group consisting of O, S, S=O, and $SO_2$; and
each $R^{40}$ is independently $C_{10}$-$C_{22}$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_8$ alkylene, or $C_1$-$C_8$ heteroalkylene.

Each heterocyclic and heteroaryl ring system is optionally substituted with $C_1$-$C_3$ alkyl, —OH, amino and carboxyl groups.

In one embodiment, the present invention utilizes the following $Y^1$ groups: $CH_2$, CHMe, CH(isopropyl), CH(tertiarybutyl), $C(Me)_2$, $C(Et)_2$, $C(isopropyl)_2$, and $C(propyl)_2$.

In another embodiment, the present invention utilizes the following $X^2$ groups:

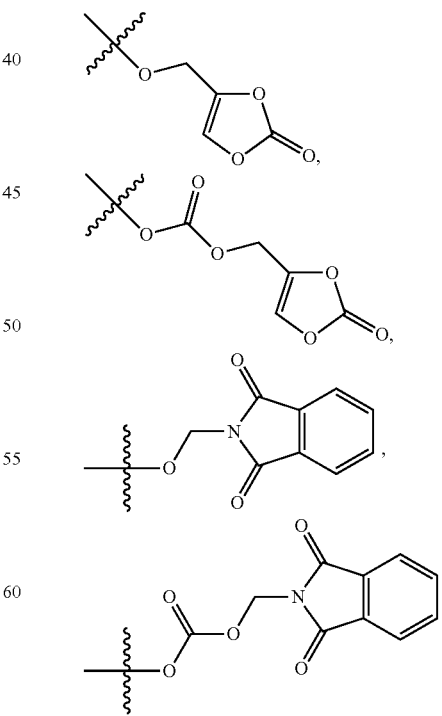

—OMe, —OEt, —O-isopropyl, O-isobutyl, —O-tertiarybutyl, —O—COMe, —O—C(=O)(isopropyl), —O—C(=O)

(isobutyl), —O—C(=O)(tertiarybutyl), —O—C(=O)—NMe$_2$, —O—C(=O)—NHMe, —O—C(=O)—NH$_2$, —O—C(=O)—N(H)—CH(R$^{41}$)—CO$_2$Et wherein R$^{41}$ is a side chain C$_1$-C$_6$ alkyl, or C$_3$-C$_9$ heterocyclyl group selected from the side chain groups present in essential amino acids; —O—P(=O)(OMe)$_2$, —O—P(=O)(O-isopropyl)$_2$, and —O—P(=O)(O-isobutyl)$_2$. Each heterocyclic is optionally substituted with one or more, preferably, 1-3, C$_1$-C$_3$ alkyl, —OH, amino and/or carboxyl groups.

In another embodiment, In one embodiment, R is:

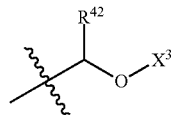

wherein

X$^3$ is independently C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl; and R$^{42}$ is independently hydrogen or C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl.

Each heterocyclic is optionally substituted with one or more, preferably, 1-3, C$_1$-C$_3$ alkyl, —OH, amino and/or carboxyl groups.

In one embodiment, R is:

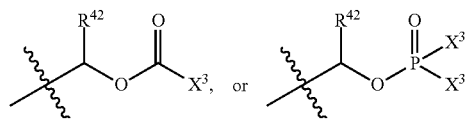

wherein each X$^3$ is independently amino, hydroxyl, mercapto, C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl, C$_1$-C$_6$ alkoxy, C$_1$-C$_6$ alkylamino, C$_1$-C$_6$ dialkylamino, C$_1$-C$_6$ alkylthio, a bile acid based alkoxy group, a sugar moiety, a PEG moiety, and —O—CH$_2$—CH(OR$^{40}$)CH$_2$X$^4$R$^{40}$, wherein:

X$^4$ is selected from the group consisting of O, S, S=O, and SO$_2$; and each R$^{40}$ is independently C$_{10}$-C$_{22}$ alkyl, C$_3$-C$_8$ cycloalkyl, C$_3$-C$_9$ heterocyclyl, C$_6$-C$_{10}$ aryl, C$_3$-C$_9$ heteroaryl, C$_1$-C$_8$ alkylene, or C$_1$-C$_8$ heteroalkylene; and R$^{42}$ is independently hydrogen or C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl.

In some embodiments, R$^{42}$ is independently hydrogen or C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl; and each X$^3$ independently is C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl, C$_1$-C$_6$ alkoxy, C$_1$-C$_6$ alkylamino, C$_1$-C$_6$ dialkylamino, or C$_1$-C$_6$ alkylthio.

In some embodiments, R is represented by the following structures:

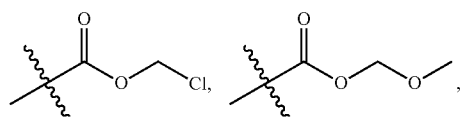

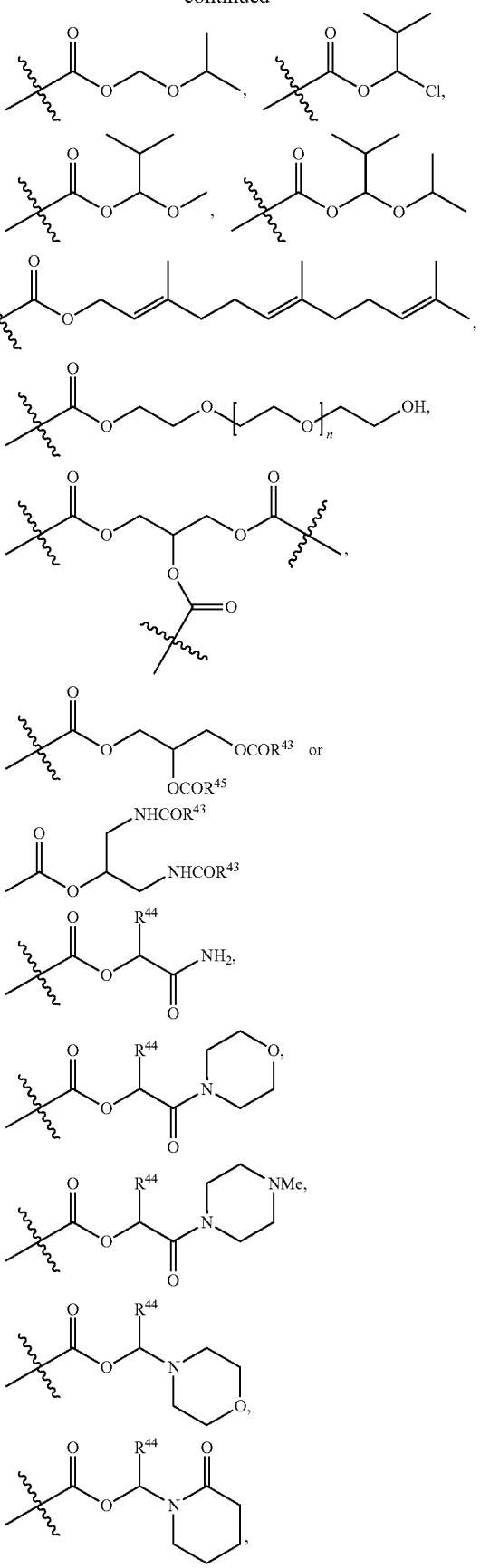

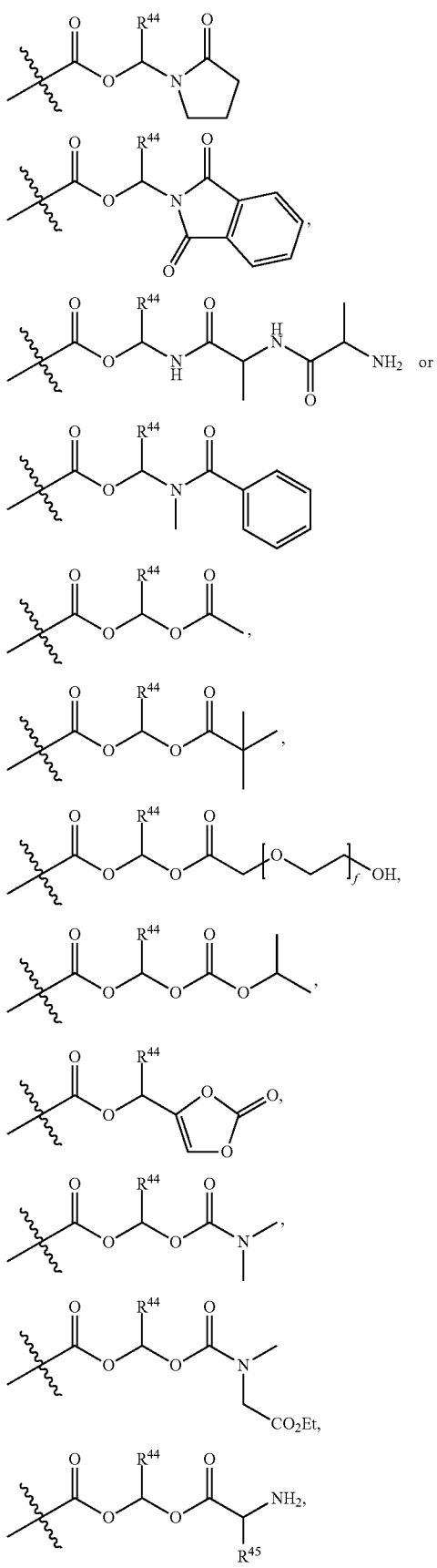

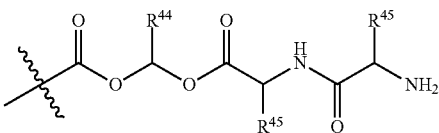

wherein, in the above examples, $R^{43}$ is $C_{10}$-$C_{22}$ alkyl or alkylene, $R^{44}$ is H or $C_1$-$C_6$ alkyl and $R^{45}$ represents side chain alkyl groups present in naturally occurring alpha amino acids;

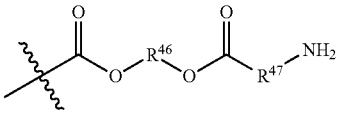

wherein $R^{46}$ is $(CH_2)_n$, f=2-4, and CO—$R^{47}$—$NH_2$ represents an aminoacyl group; or

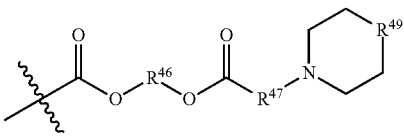

wherein $R^{46}$ is $(CH_2)_n$, n=2-4, $R^{47}$ is $(CH_2)_n$, n=1-3 and $R^{49}$ is O or NMe.

In one embodiment, R is:

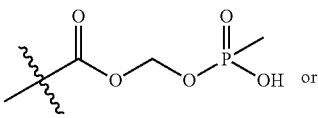

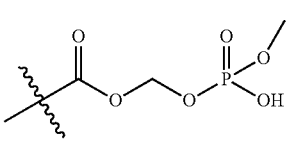

In one aspect, R is —C($R^{200}R^{201}$)O($R^{202}R^{203}$)P(O)O$R^{204}$N$R^{205}R^{206}$, wherein each $R^{200}$, $R^{201}$, $R^{202}$, $R^{203}$, $R^{204}$, $R^{205}$ and $R^{206}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl, wherein each alkyl, heterocyclyl, cycloalkyl, aryl, and heteroaryl is optionally substituted.

In some embodiments, R is —CH($R^{201}$)OCH$_2$P(O)O$R^{204}$NH$R^{206}$, wherein $R^{201}$ is $C_1$-$C_8$ alkyl, $R^{204}$ is phenyl, optionally substituted. In one embodiment, $R^{206}$ is —CH$R^{207}$C(O)O$R^{208}$ wherein $R^{207}$ is selected from the group consisting of the naturally occurring amino acid side chains and CO$_2$H esters thereof and $R^{208}$ is $C_1$-$C_8$ alkyl. In one embodiment, $R^{206}$ is $C_1$-$C_6$ alkyl, optionally substituted with 1-3, CO$_2$H, SH, NH$_2$, $C_6$-$C_{10}$ aryl, and $C_2$-$C_{10}$ heteroaryl.

In some embodiments, R is:

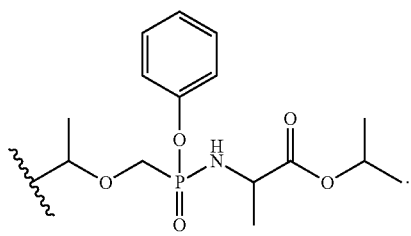 [SMILES: *C(C)OCP(=O)(NC(C)C(=O)OC(C)C)Oc1ccccc1]

In one embodiment, R is:

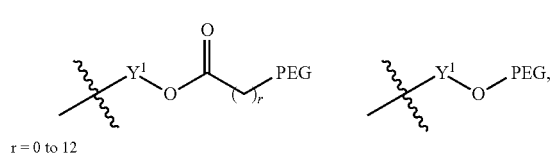

r = 0 to 12 or
wherein $Y^1$ is —C($R^{38}$)$_2$, wherein each $R^{38}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Various polyethylene glycol (PEG) moieties and synthetic methods related to them that can be used or adapted to make compounds of the invention are described in U.S. Pat. Nos. 6,608,076; 6,395,266; 6,194,580; 6,153,655; 6,127,355; 6,111,107; 5,965,566; 5,880,131; 5,840,900; 6,011,042 and 5,681,567.

In one embodiment, R is

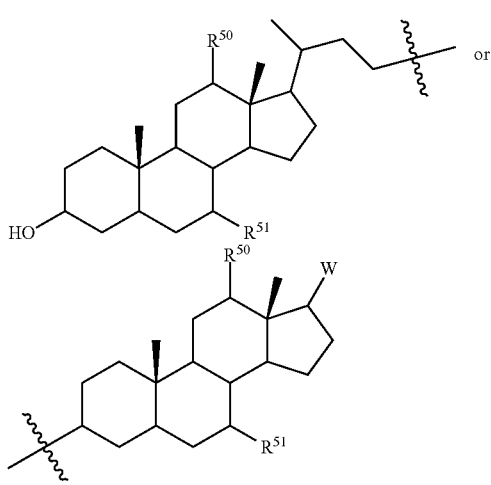

wherein
$R^{50}$ is —OH or hydrogen;
$R^{51}$ is —OH, or hydrogen;
W is —CH(CH$_3$)W$^1$;
wherein W$^1$ is a substituted $C_1$-$C_8$ alkyl group containing a moiety which is optionally negatively charged at physiological pH,
said moiety is selected from the group consisting of CO$_2$H, SO$_3$H, SO$_2$H, —P(O)(OR$^{52}$)(OH), —OP(O)(OR$^{52}$)(OH), and OSO$_3$H,
wherein $R^{52}$ is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Each heterocyclic and heteroaryl ring system is optionally substituted with one or more, preferably 1-3, $C_1$-$C_3$ alkyl, —OH, amino and/or carboxyl groups.

In one embodiment, R is:

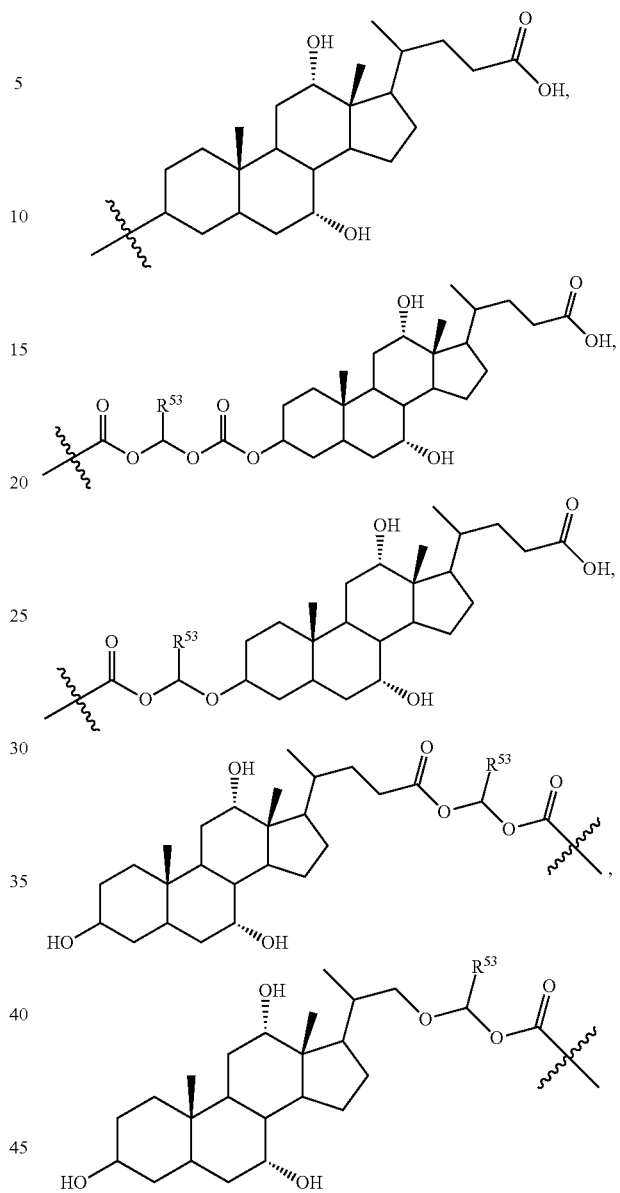

wherein $R^{53}$ is H or $C_1$-$C_6$ alkyl.

In another aspect, R is SO$_3$H.

In another aspect, R comprises a cleavable linker, wherein the term "cleavable linker" refers to a linker which has a short half life in vivo. The breakdown of the linker Z in a compound releases or generates the active compound. In one embodiment, the cleavable linker has a half life of less than ten hours. In one embodiment, the cleavable linker has a half life of less than an hour. In one embodiment, the half life of the cleavable linker is between one and fifteen minutes. In one embodiment, the cleavable linker has at least one connection with the structure: C*—C(=X*)X*—C* wherein C* is a substituted or unsubstituted methylene group, and X* is S or O. In one embodiment, the cleavable linker has at least one C*—C(=O)O—C* connection. In one embodiment, the cleavable linker has at least one C*—C(=O)S—C* connection. In one embodiment, the cleavable linker has at least one —C(=O)N*—C*—SO$_2$-N*-connection, wherein N* is —NH— or $C_1$-$C_6$ alkylamino. In one embodiment, the cleavable linker is hydrolyzed by an esterase enzyme.

In one embodiment, the linker is a self-immolating linker, such as that disclosed in U.S. patent publication 2002/0147138, to Firestone; PCT Appl. No. US05/08161 and PCT Pub. No. 2004/087075. In another embodiment, the linker is a substrate for enzymes. See generally Rooseboom et al., 2004, Pharmacol. Rev. 56:53-102.

Pharmaceutical Compositions

In further aspects of the invention, a composition is provided comprising any of the compounds described herein, and at least a pharmaceutically acceptable excipient.

In another aspect, this invention provides a composition comprising any of the compounds described herein, and a pharmaceutically acceptable excipient.

Such compositions can be formulated for different routes of administration. Although compositions suitable for oral delivery will probably be used most frequently, other routes that may be used include transdermal, intravenous, intraarterial, pulmonary, rectal, nasal, vaginal, lingual, intramuscular, intraperitoneal, intracutaneous, intracranial, and subcutaneous routes. Suitable dosage forms for administering any of the compounds described herein include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16$^{th}$ ed., A. Oslo editor, Easton Pa. 1980).

Pharmaceutically acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

In one embodiment, this invention provides sustained release formulations such as drug depots or patches comprising an effective amount of a compound provided herein. In another embodiment, the patch further comprises gum Arabic or hydroxypropyl cellulose separately or in combination, in the presence of alpha-tocopherol. Preferably, the hydroxypropyl cellulose has an average MW of from 10,000 to 100,000. In a more preferred embodiment, the hydroxypropyl cellulose has an average MW of from 5,000 to 50,000.

Compounds and pharmaceutical compositions of this invention maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

Methods of Treatment

In aspects of the invention, a method is provided for increasing tissue and/or cellular oxygenation, the method comprising administering to a subject in need thereof a therapeutically effective amount of any of the compounds or compositions described herein.

In aspects of the invention, a method is provided for increasing oxygen affinity of hemoglobin S in a subject, the method comprising administering to a subject in need thereof a therapeutically effective amount of any of the compounds or compositions described herein.

In aspects of the invention, a method is provided for treating a condition associated with oxygen deficiency, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

In further aspects of the invention, a method is provided for treating sickle cell disease, the method comprising administering to a subject in need thereof a therapeutically effective amount of a compound of any of the compounds or compositions described herein. In still further aspects of the invention, a method is provided for treating cancer, a pulmonary disorder, stroke, high altitude sickness, an ulcer, a pressure sore, Alzheimer's disease, acute respiratory disease syndrome, and a wound, the method comprising administering to a subject in need thereof a therapeutically effective amount of a compound of any of the compounds or compositions described herein.

Synthetic Methods

Certain methods for making the compounds described herein are also provided. The reactions are preferably carried out in a suitable inert solvent that will be apparent to the skilled artisan upon reading this disclosure, for a sufficient period of time to ensure substantial completion of the reaction as observed by thin layer chromatography, $^1$H-NMR, etc. If needed to speed up the reaction, the reaction mixture can be heated, as is well known to the skilled artisan. The final and the intermediate compounds are purified, if necessary, by various art known methods such as crystallization, precipitation, column chromatography, and the likes, as will be apparent to the skilled artisan upon reading this disclosure.

An illustrative and non-limiting method for synthesizing a compound of formula (I), is schematically shown below.

In the following Schemes,

refer to rings A, B and C as described herein.

X and X$^5$ each represent a leaving group and are independently selected from Cl, F, Br, and I.

$X^6$ represents $CHR^{14}$, $NR^{14}$, O, S(O)x; wherein x is 0, 1, or 2;

$Y^5$ represents a leaving group selected from Cl, F, Br, I, $OSO_2R^{17}$ and $OSO_2Ar$;

$R^{17}$ is $C_1$-$C_6$ alkyl;

n is 0, 1, or 2;

Ar is phenyl optionally substituted with 1-3 halo or $C_1$-$C_4$ alkyl groups.

Where variables already used in the structures hereinabove are used in the shcemes, the context makes it unambiguous as to what the variable refers to.

General Synthetic Scheme 1A

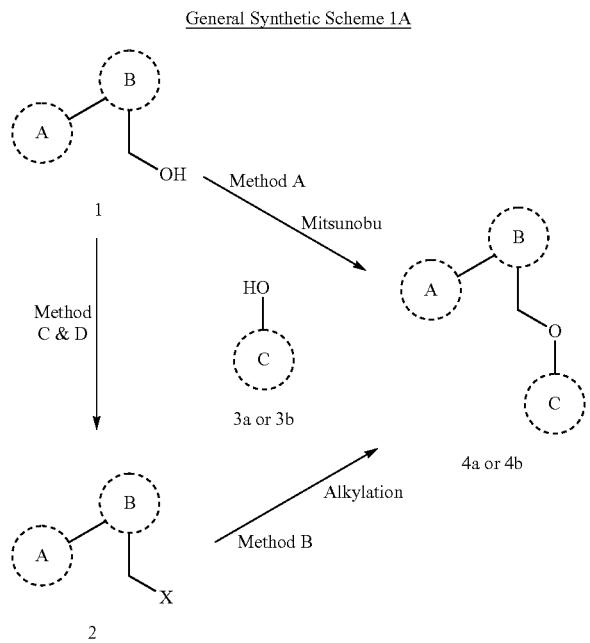

General Method A for Preparing Aryloxy Ether Analogs (4a) from Substituted Methylene Alcohol (1) and Hydroxyl Aryl Aldehyde Derivative (3a).

A hydroxyl arylaldehyde derivative (3a) (0.1-2 mmol) mixture with substituted methylene alcohol (1) (0.8 to 1.2eq) and $PPh_3$ (1-1.5eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was stirred for 10 min, then filtered through a pad of silica. The silica was washed with ethyl acetate 2-20 mL. The combined filtrates were evaporated and the residue was dried on highvac. The residue was purified by preparative HPLC or flash silica gel chromatography.

General Method B for Preparing Aryloxy Ether Analogs (4a) from Substituted Methylene Halide (2) and Hydroxyl Aryl Aldehyde Derivatives (3a).

A mixture of hydroxyl arylaldehyde derivatives (3a) (0.1-2 mmol, 1-4 eq.), substituted methylene chloride or bromide (2) (1eq), and $K_2CO_3$ (2-5 eq.) (catalytic amount of NaI or $Bu_4NI$ may also be added) in DMF or acetonitrile (1 to 10 mL) was stirred at RT or heating up to 120° C. for 0.5-8 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvents mixture (e.g., ethyl acetate/hexanes).

General Method C for Preparing Substituted Methylene Chloride (2a).

To a solution of substituted methylene alcohol (1) (0.1 to 2 mmol) in DCM (1-10 mL) was added $SOCl_2$ dropwise (2eq to 5eq) at 0° C. or RT. The reaction mixture was stirred at RT for 10 min to 6 h, or until reaction is judged complete (LC/MS). The reaction mixture is concentrated to dryness over a rotavap. The crude chloride residue was suspended in toluene, sonicated and concentrated to dryness. The process was repeated three times and dried under vacuum to give the substituted methylene chloride (2), usually as an off-white solid, which was used for next step without further purification. Alternatively, a solution of aqueous 1N $Na_2CO_3$ is then added to produce a solution of pH~8. the mixture was extracted with DCM (3×10-50 mL), dried over sodium sulfate, and concentrated to the crude substituted methylene chloride (2a), which is then purified by column chromatography on silica gel (0-100% ethyl acetate-hexanes).

General Method D for Preparing Substituted Methylene Bromide (2b).

To a solution of substituted methylene alcohol (1) (0.1 to 2 mmol) in DCM (1-10 mL) was added $Ph_3PBr_2$ dropwise (2eq to 5eq) at 0° C. or RT. The reaction mixture was stirred at RT for 10 min to 2 h, or until reaction is judged complete (LC/MS). The reaction mixture is concentrated to dryness over a rotavap. The residue purified by column chromatography on silica gel (0-100% ethyl acetate-hexanes) to afford the pure bromide 2b.

Similarly, N-linked heterocyclic analogs (compound 5) can also be synthesized from amination procedures developed by Buchwald and Hartwig.

Scheme 1B

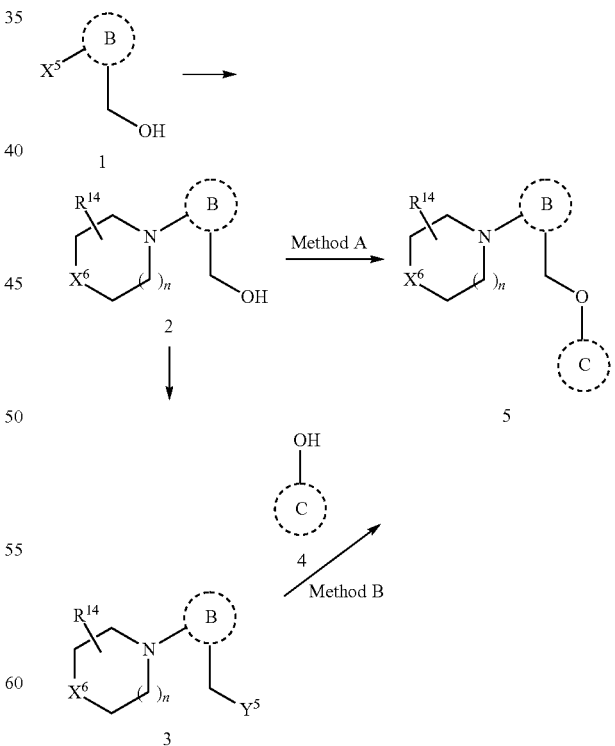

Protected amides of formula $-CONHR^{95}$ and $-CONHOR^{95}$ can be converted e.g., hydrolyzed to the corresponding amides according to methods known to the skilled artisan. $C_{19}H_{23}N_3O_3$: 342.2.

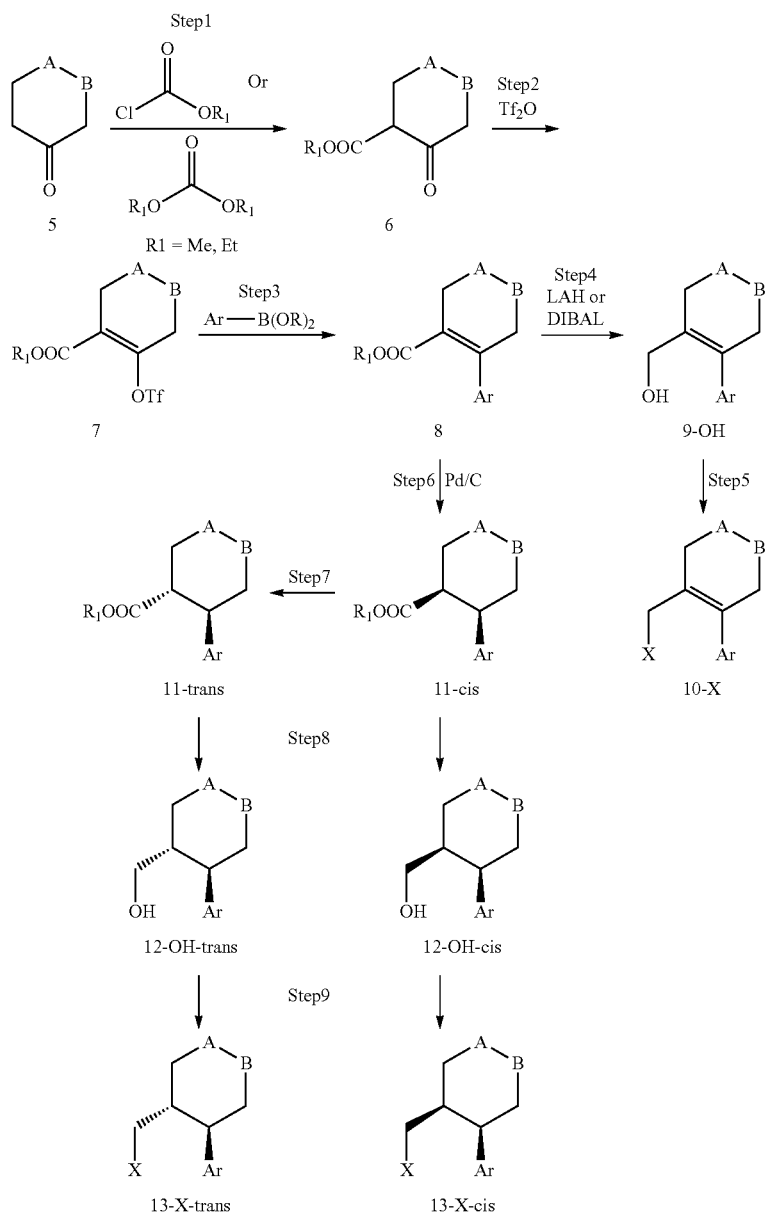

General Method E (Scheme 2) for Preparing Heterocyclic Methylene Derivatives 9, 10, 12 and 13.

Condensation of heterocyclic ketone analog 5 with chloroformate or dialkyl carbonate gives (hetero)cyclic beta-ketone ester 6 (Step 1). The ketone ester 6 is converted to the triflate intermediate 7 by treating with a triflating agent (e.g., triflic anhydride) in the presence of an organic base such as Hunig's base (Step 2). Suzuki coupling of the triflate 7 with a boronic acid or ester affords heterocyclohexene carboxylate 8 (Step 3). Subsequent reduction of the ester group by LAH or DIBAL gives the corresponding alcohol 9-OH (Step 4). Further reaction of the alcohol 9-OH with thionyl chloride, Ph₃PBr₂ (or CBr₄—Ph₃P or PBr₃), or alkyl/aryl sufonyl chloride produces the corresponding 10-X chloride, bromide or sulfonate (Step 5).

Alternatively, the double bond of heterocyclohexene carboxylate 8 is reduced to give the cis-heterocyclohexane 11-cis carboxylate under palladium catalyzed hydrogenation conditions (Step 6). Reduction of the ester group of 11-cis by LAH or DIBAL yields cis-alcohol 12-OH-cis (Step 8). Conversion of the alcohol 12-OH-cis to its chloride, bromide or sulfonate (such as mesylate, tosylate) 13-X-cis can be achieved by reacting with thionyl chloride, or Ph₃PBr₂, or sufonyl chloride (such as mesyl chloride or tosyl chloride) (Step 9). The cis-cyclohexane carboxylate 11-cis can also be isomerized to the thermodynamically more stable trans-isomer 11-trans by the treatment with an alcoholic alkoxide (e.g., ethoxide) solution. Analogously, transformation of 11-trans ester to 12-trans alcohol and 13-X-trans halide is accomplished by applying conditions of Step 8 and Step 9 (Scheme 2) similar to these for the corresponding cis-isomers.

Scheme 3

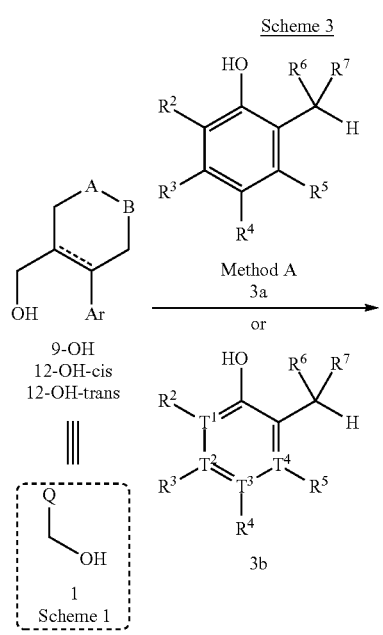

9-OH
12-OH-cis
12-OH-trans

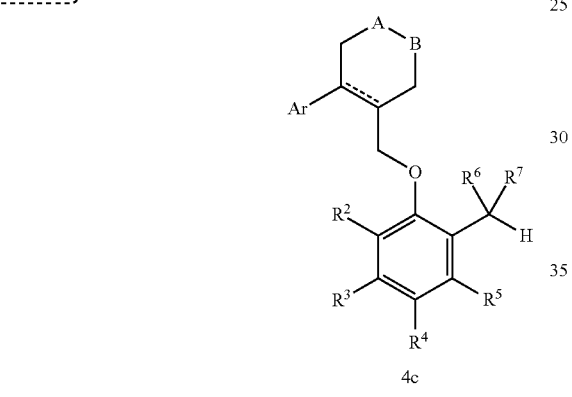

4c

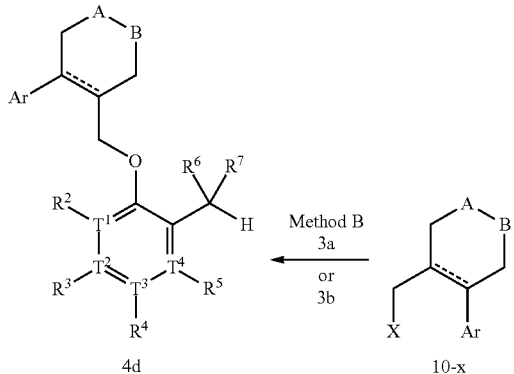

4d

Coupling of the (hetero)cyclic methylene derivatives 9, 10, 12 and 13 with hydroxyl (hetero)arylaldehyde derivatives (3a/3b) (see, e.g., Scheme 3) by general method A or B affords the corresponding aryloxy/heteroarylether analogs (4c and 4d).

General Synthetic Scheme 4

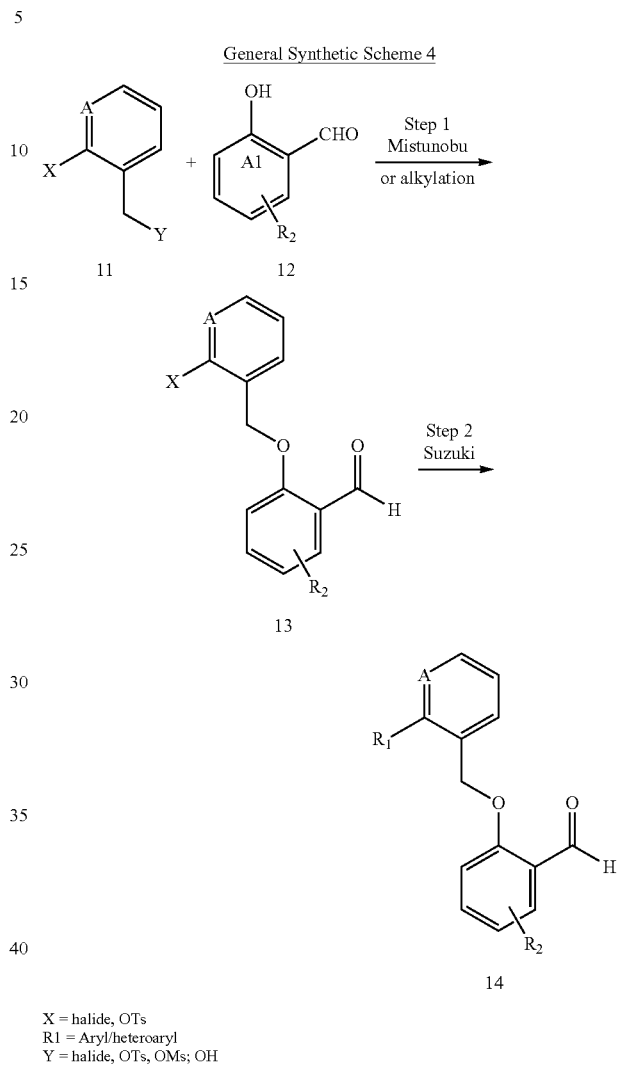

X = halide, OTs
R1 = Aryl/heteroaryl
Y = halide, OTs, OMs; OH

Step 1a-Compound 13 can is synthesized via O-alkylation of phenol aldehyde 12 with alkyl halide 11 (Y=halide, OTs, OMs). A mixture of hydroxyl (hetero)arylaldehyde derivatives (12) (0.1-2 mmol, 1-4 eq.), substituted methylene chloride or bromide (11) (1eq), and $K_2CO_3$ (2-5 eq.) (catalytic amount of NaI or $Bu_4NI$ may also be added) in DMF, acetonitrile, NMP or DMSO (1 to 10 mL) was stirred at RT or heating up to 120° C. for 1-24 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvents mixture (e.g., ethyl acetate/hexanes).

Step 1b—Alternatively, compound 13 is made by coupling of phenol aldehyde 12 with alcohol 1 (Y=OH) under Mitsunobu conditions. A hydroxyl (hetero)arylaldehyde derivatives (12) (0.1-2 mmol) mixture with substituted methylene alcohol (11, Y=OH) (0.8 to 1.2eq) and (polymer-supported)/PPh$_3$ (1-1.5eq) in anhydrous THF (1-10 mL) was stirred under nitrogen until complete dissolution. The solution was cooled to 0° C. on ice bath and DIAD or DEAD (1.1 eq) in THF or toluene was added drop wise over a 1-20 min period. The ice cooling bath was allowed to expire over 90 min and the mixture was stirred at RT for 2-48 hours. The mixture was stirred for 10 min, then filtered through a pad of silica. The silica was washed with ethyl acetate 2-20 mL. The combined filtrates were evaporated and the residue was dried on highvac. The residue was purified by preparative HPLC or flash silica gel chromatography.

Step 2. To a solution of (2-chloropyridin-3-yl)methanol or (2-bromopyridin-3-yl)methanol (1-100 mmol) and appreciate bronic acid or ester (0.8 to 1.5 eq) in dioxane (2-200 mL) was added a solution of sodium bicarbonate (3 eq) in water (1-100 mL), followed by the addition of Pd(dppf)Cl$_2$ (5 to 10 mol %). After heating at 100° C. for 4-24 h, the reaction mixture was cooled and diluted with EtOAc, organic layer was washed with water, brine, dried and concentrated to give crude product, which was purified by column chromatography.

hydroxymethylene derivative 22 (step 1). The final product can be synthesized via either direct Mitsunobu reaction of 22 with phenol aldehyde 24 or conversion of the alcohol 22 to halide 23 followed by O-alkylation of phenol 24 with 23.

Prodrug Synthesis

Syntheses of the ester prodrugs start with the free carboxylic acid bearing the tertiary amine. The free acid is activated for ester formation in an aprotic solvent and then reacted with a free alcohol group in the presence of an inert base, such as triethyl amine, to provide the ester prodrug. Activating conditions for the carboxylic acid include forming the acid chloride using oxalyl chloride or thionyl chloride in an aprotic solvent, optionally with a catalytic amount of dimethyl formamide, followed by evaporation. Examples of aprotic solvents, include, but are not limited to methylene chloride, tetrahydrofuran, and the like. Alternatively, activations can be performed in situ by using reagents such as BOP (benzotriazol-1-yloxytris(dimethylamino) phosphonium hexafluorolphosphate, and the like (see Nagy et al., 1993, Proc. Natl. Acad. Sci. USA 90:6373-6376) followed by reaction with the free alcohol. Isolation of the ester products can be affected by extraction with an organic solvent, such as ethyl acetate or methylene chloride, against a mildly acidic aqueous solution; followed by base treatment of the acidic aqueous phase so as to render it basic; followed

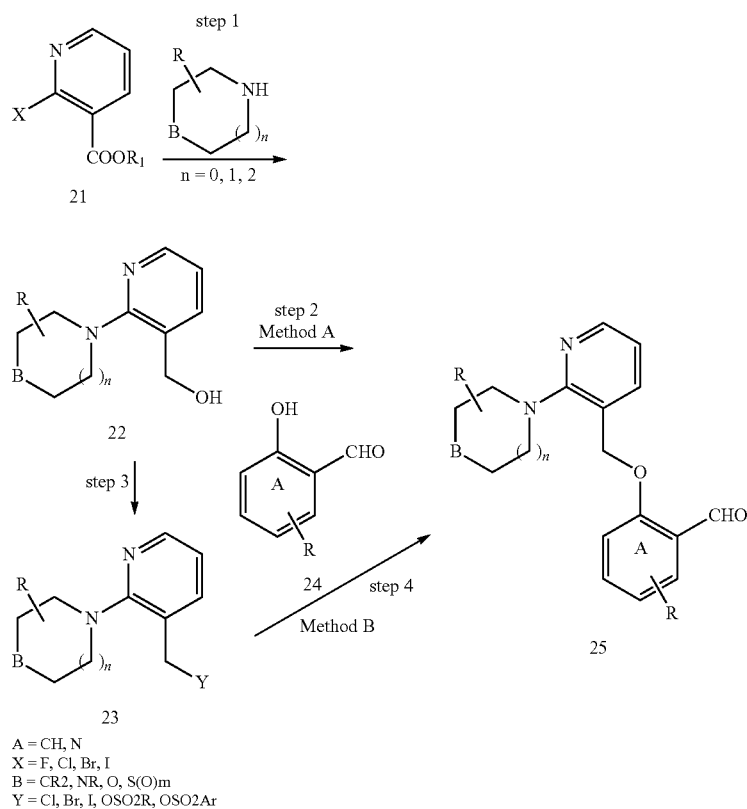

General Synthetic Scheme 5

A = CH, N
X = F, Cl, Br, I
B = CR2, NR, O, S(O)m
Y = Cl, Br, I, OSO2R, OSO2Ar

Compound 25 can be prepared from 2-halonicotinate through a series organic transformations that involve displacement with cyclic amine and reduction of ester to give by extraction with an organic solvent, for example ethyl acetate or methylene chloride; evaporation of the organic solvent layer; and recrystalization from a solvent, such as ethanol. Optionally, the solvent can be acidified with an acid, such as HCl or acetic acid to provide a pharmaceutically acceptable salt thereof. Alternatively the crude reaction can be passed over an ion exchange column bearing sulfonic acid groups in the protonated form, washed with deionized water, and eluted with aqueous ammonia; followed by evaporation.

Suitable free acids bearing the tertiary amine are commercially available, such as 2-(N-morpholino)-propionic acid, N,N-dimethyl-beta-alanine, and the like. Non-commercial acids can be synthesized in straightforward manner via standard literature procedures.

Carbonate and carbamate prodrugs can be prepared in an analogous way. For example, amino alcohols and diamines can be activated using activating agents such as phosgene or carbonyl diimidazole, to provide an activated carbonates, which in turn can react with the alcohol and/or the phenolic hydroxy group on the compounds utilized herein to provide carbonate and carbamate prodrugs.

Various protecting groups and synthetic methods related to them that can be used or adapted to make compounds of the invention can be adapted from the references Testa et al., Hydrolysis in Drug and Prodrug Metabolism, June 2003, Wiley-VCH, Zurich, 419-534 and Beaumont et al., Curr. Drug Metab. 2003, 4:461-85.

Provided herein is a method of synthesizing an acyloxymethyl version of a prodrug by adapting a method from the reference Sobolev et al., 2002, J. Org. Chem. 67:401-410.

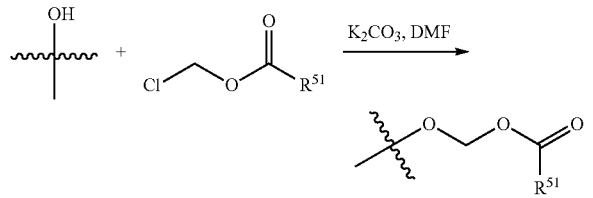

$R^{51}$ is $C_1$-$C_6$ alkyl.

Provided herein is a method for synthesizing a phosphonooxymethyl version of a prodrug by adapting a method from Mantyla et al., 2004, J. Med. Chem. 47:188-195.

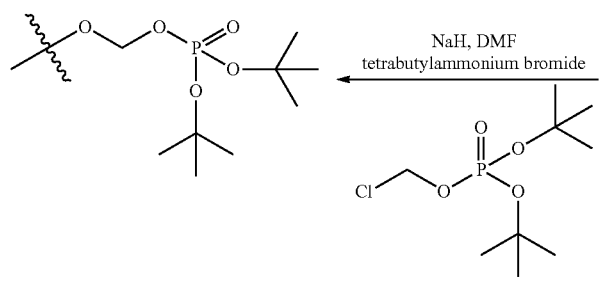

Provided herein is a method of synthesizing an alkyloxymethyl version of a prodrug

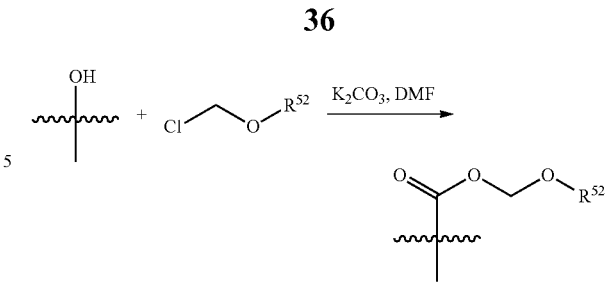

$R^{52}$ is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

In the examples below as well as throughout the application, the following abbreviations have the following meanings. If not defined, the terms have their generally accepted meanings.

° C.=degrees Celsius
RT=Room temperature
min=minute(s)
h=hour(s)
µL=Microliter
mL=Milliliter
mmol=Millimole
eq=Equivalent
mg=Milligram
MS=Mass spectrometry
LC-MS=Liquid chromatography-mass spectrometry
HPLC=High performance liquid chromatography
NMR=Nuclear magnetic resonance
EtOAc=Ethyl acetate
Ph$_3$PBr$_2$=Triphenylphosphine dibromide
DMF=N, N-Dimethylformamide
DCM=Dichloromethane
DMSO=Dimethyl sulfoxide
THF=Tetrahydrofuran

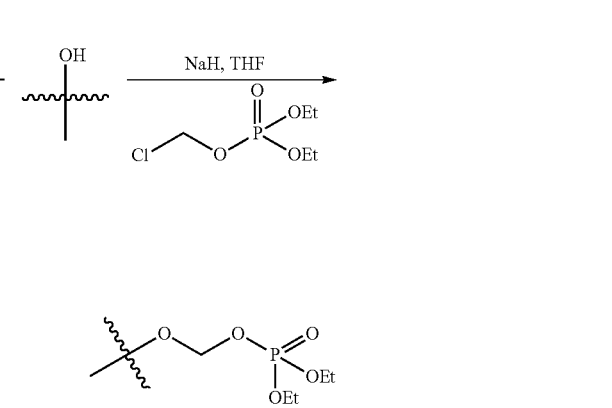

DIAD=Diisopropyl azodicarboxylate
DEAD=Diethyl azodicarboxylate

Preparation of 2-[[2-[(3R)-3-fluoropyrrolidin-1-yl]pyridin-3-yl]methoxy]-6-hydroxybenzaldehyde

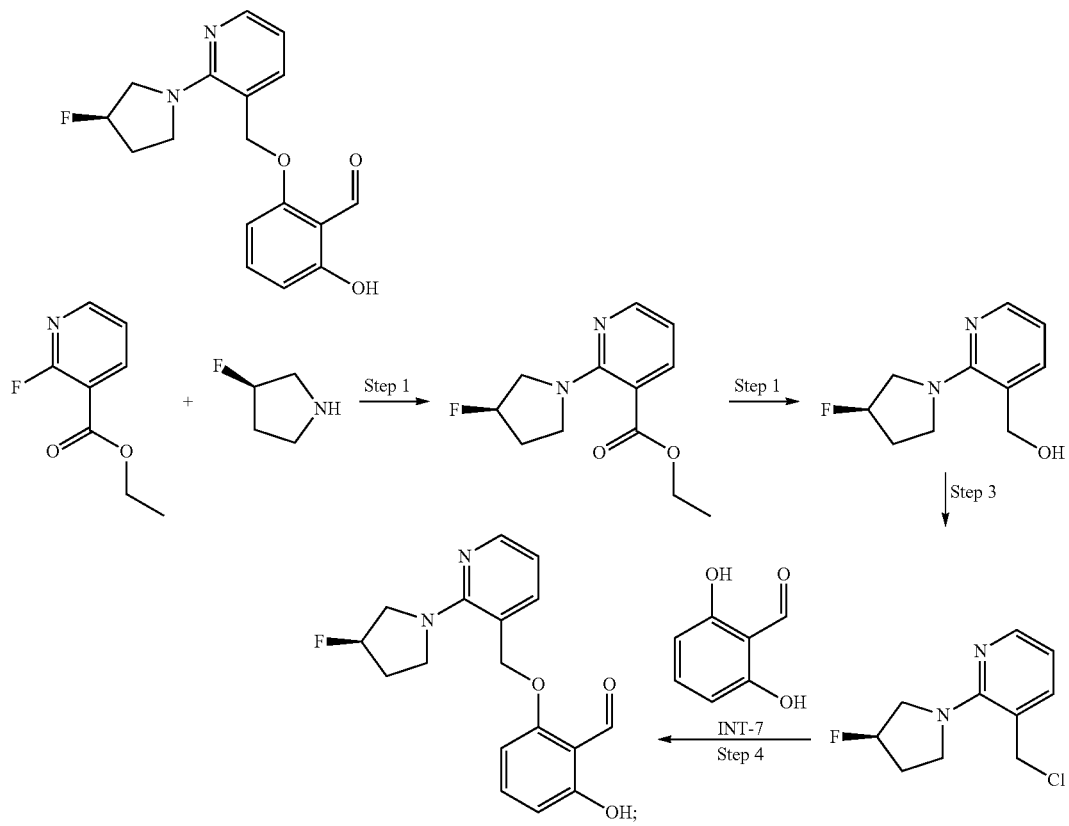

Step 1: (R)-ethyl 2-(3-fluoropyrrolidin-1-yl)nicotinate. To a solution of ethyl 2-fluoronicotinate (0.074 g, 0.48 mmol) in DMF (0.3 mL) was added diisopropylethyl amine (0.25 mL, 1.4 mmol), and (R)-3-fluoropyrrolidine (0.090 g, 0.72 mmol). The resulting mixture was irradiated with microwaves (100° C.) for 1 h and loaded directly onto a silica column. Eluting the column with EtOAc/hexanes (0-100%) provided (R)-ethyl 2-(3-fluoropyrrolidin-1-yl)nicotinate as a clear oil (0.100 g, 94% yield); MS (ESI) m/z 239 [M+H]$^+$.

Step 2: (R)-(2-(3-fluoropyrrolidin-1-yl)pyridin-3-yl)methanol. To a cooled (0° C.) solution of (R)-methyl 2-(3-fluoropyrrolidin-1-yl)nicotinate in THF (5 mL) was added a solution of lithium aluminum hydride (1M in THF). The reaction mixture was stirred for 1 h and then 20 μL of H$_2$O was added followed by 20 μL of 15% NaOH (aq) and then 60 μL of additional water. The slurry was stirred for 1 h and filtered and the resulting residue was washed with ether. The combined organic layers were dried over MgSO$_4$ and concentrated in vacuo. Purification by column chromotography (EtOAc/hexanes, 0-100%) provided (R)-(2-(3-fluoropyrrolidin-1-yl)pyridin-3-yl)methanol (0.081 g, 92% yield). MS (ESI) m/z 197 [M+H]+.

Step 3: (R)-3-(chloromethyl)-2-(3-fluoropyrrolidin-1-yl)pyridine. To a cooled (0° C.) solution of (R)-(2-(3-fluoropyrrolidin-1-yl)pyridin-3-yl)methanol (0.081 g, 0.38 mmol) in dichloromethane was added SOCl$_2$ (0.450 g, 3.8 mmol) and the reaction mixture was allowed to warm to ambient temperature. After 1 h, the reaction mixture was concentrated and azeotroped with toluene to provide (R)-3-(chloromethyl)-2-(3-fluoropyrrolidin-1-yl)pyridine (0.080 g, 92%) as a clear oil. MS (ESI) m/z 215 [M+H]$^+$.

Step 4: (R)-2-((2-(3-fluoropyrrolidin-1-yl)pyridin-3-yl)methoxy)-6-hydroxybenzaldehyde. To a solution of (R)-3-(chloromethyl)-2-(3-fluoropyrrolidin-1-yl)pyridine (0.080 g, 0.35 mmol) and 2,6-dihydroxybenzaldehyde (0.130 g, 0.94 mmol) in DMF was added potassium carbonate (0.190 g, 1.4 mmol) and the reaction mixture was heated (60° C.). After 30 minutes, the DMF was removed and the resulting residue was reconstituted in CH$_2$Cl$_2$ and filtered through a plug of silica (EtOAc/hexanes, 1:1). Purification Prep-HPLC provided (R)-2-((2-(3-fluoropyrrolidin-1-yl)pyridin-3-yl)methoxy)-6-hydroxybenzaldehyde (8 mg, 5% yield). $^1$H NMR (400 MHz, DMSO-d$_6$) δ 11.71 (dd, J=8.4, 0.7 Hz, 1H), 10.21 (d, J=0.5 Hz, 1H), 8.10 (dd, J=4.8, 1.9 Hz, 1H), 7.71 (dd, J=7.4, 1.9 Hz, 1H), 7.52 (t, J=8.4 Hz, 1H), 6.73 (dd, J=8.6, 0.7 Hz, 1H), 6.71 (dd, J=7.4, 5.0 Hz, 1H), 6.53 (dt, J=8.4, 0.7 Hz, 1H), 5.40 (dd, J=54.2, 3.3 Hz, 1H), 5.28 (d, J=11.3 Hz, 1H), 5.17 (d, J=12.0 Hz, 1H), 3.91-3.56 (m, 4H), 2.21-1.93 (m, 2H); MS (ESI) m/z 317 [M+H]+.

GBT883

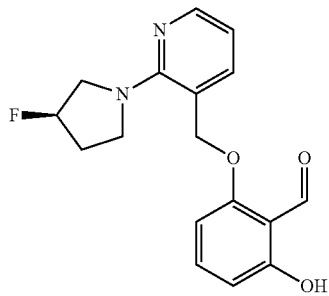 [SMILES: O=Cc1c(O)cccc1OCc1cccnc1N1CC[C@@H](F)C1]

GBT883—(R)-2-((2-(3-fluoropyrrolidin-1-yl)pyridin-3-yl)methoxy)-6-hydroxybenzaldehyde. The compound was prepared from ethyl 2-fluoronicotinate and (R)-3-fluoropyrrolidine according to scheme 5, reaction steps 1, 3 and 4.

Step 1a: To a solution of ethyl 2-fluoronicotinate (0.074 g, 0.48 mmol) in DMF (0.3 mL) was added diisopropylethyl amine (0.25 mL, 1.4 mmol), and (R)-3-fluoropyrrolidine (0.090 g, 0.72 mmol). The resulting mixture was irradiated with microwaves (100° C.) for 1 h and loaded directly onto a silica column. Eluting the column with EtOAc/hexanes (0-100%) provided (R)-ethyl 2-(3-fluoropyrrolidin-1-yl)nicotinate as a clear oil (0.100 g, 94% yield). MS (ES) for $C_{12}H_{15}FN_2O_2$: 225 (MH$^+$).

Step 1b: To a cooled (0° C.) solution of (R)-methyl 2-(3-fluoropyrrolidin-1-yl)nicotinate in THF (5 mL) was added a solution of lithium aluminum hydride (1M in THF). The reaction mixture was stirred for 1 h and then 20 µL of H2O was added followed by 20 µL of 15% NaOH (aq) and then 60 µL of additional water. The slurry was stirred for 1 h and filtered and the resulting residue was washed with ether. The combined organic layers were dried over MgSO$_4$ and concentrated in vacuo. Purification by column chromotography (EtOAc/hexanes, 0-100%) provided (R)-(2-(3-fluoropyrrolidin-1-yl)pyridin-3-yl)methanol (0.081 g, 92% yield). MS (ES) for $C_{10}H_{13}FN_2O$: 197 (MH$^+$).

Step 3: To a cooled (0° C.) solution of (R)-(2-(3-fluoropyrrolidin-1-yl)pyridin-3-yl)methanol (0.081 g, 0.38 mmol) in dichloromethane was added SOCl$_2$ (0.450 g, 3.8 mmol) and the reaction mixture was allowed to warm to ambient temperature. After 1 h, the reaction mixture was concentrated and azeotroped with toluene to provide (R)-3-(chloromethyl)-2-(3-fluoropyrrolidin-1-yl)pyridine (0.080 g, 92%) as a clear oil. MS (ES) for $C_{10}H_{12}ClFN_2$: 215 (MH$^+$).

Step 4. To a solution of (R)-3-(chloromethyl)-2-(3-fluoropyrrolidin-1-yl)pyridine (0.080 g, 0.35 mmol) and 2,6-dihydroxybenzaldehyde (0.130 g, 0.94 mmol) in DMF was added potassium carbonate (0.190 g, 1.4 mmol) and the reaction mixture was heated (60° C.). After 30 minutes, the DMF was removed and the resulting residue was reconstituted in CH$_2$Cl$_2$ and filtered through a plug of silica (EtOAc/hexanes, 1:1). Purification Prep-HPLC provided (R)-2-((2-(3-fluoropyrrolidin-1-yl)pyridin-3-yl)methoxy)-6-hydroxybenzaldehyde (8 mg, 5% yield). $^1$H NMR (400 MHz, DMSO-d$_6$) δ 11.71 (dd, J=8.4, 0.7 Hz, 1H), 10.21 (d, J=0.5 Hz, 1H), 8.10 (dd, J=4.8, 1.9 Hz, 1H), 7.71 (dd, J=7.4, 1.9 Hz, 1H), 7.52 (t, J=8.4 Hz, 1H), 6.73 (dd, J=8.6, 0.7 Hz, 1H), 6.71 (dd, J=7.4, 5.0 Hz, 1H), 6.53 (dt, J=8.4, 0.7 Hz, 1H), 5.40 (dd, J=54.2, 3.3 Hz, 1H), 5.28 (d, J=11.3 Hz, 1H), 5.17 (d, J=12.0 Hz, 1H), 3.91-3.56 (m, 4H), 2.21-1.93 (m, 2H). MS (ES) for $C_{17}H_{17}FN_2O_3$: 317 (MH$^+$).

GBT910

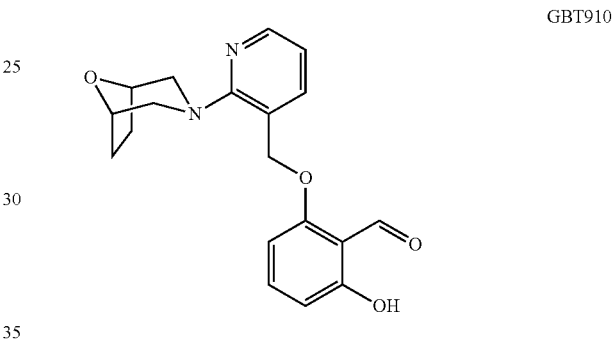

GBT910

GBT910—2-((2-(8-oxa-3-azabicyclo[3.2.1]octan-3-yl)pyridin-3-yl)methoxy)-6-hydroxybenzaldehyde. The compound was prepared from ethyl 2-fluoronicotinate and 8-oxa-3-azabicyclo[3.2.1]octane according to reaction scheme below.

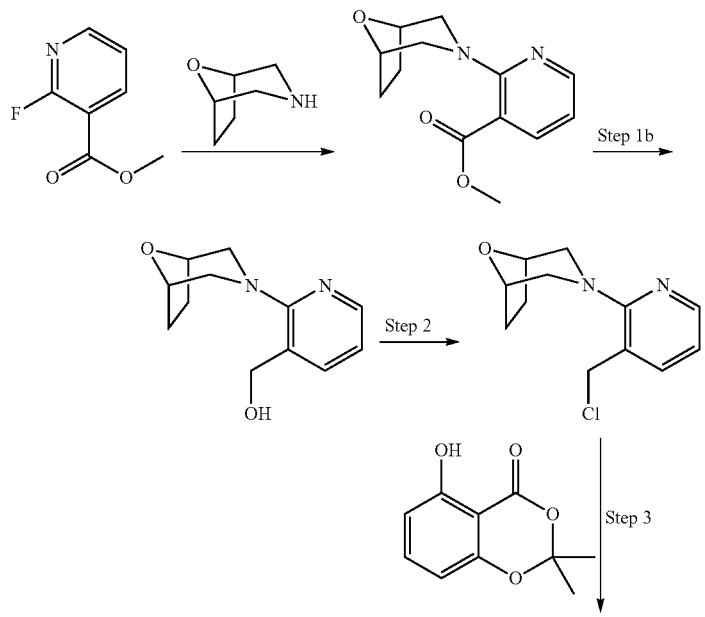

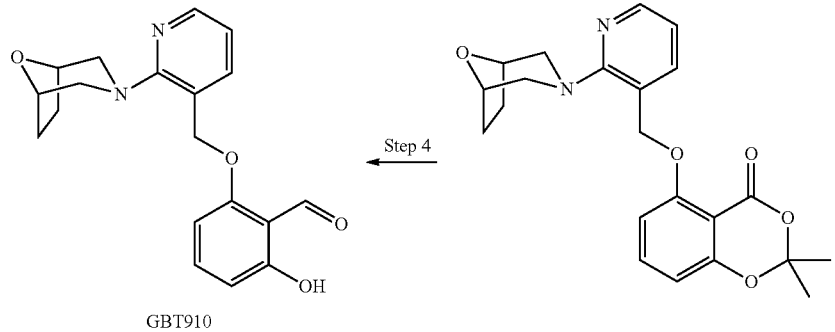

GBT910

Step 1a: To a solution of ethyl 2-fluoronicotinate (0.15 g, 0.97 mmol) in NMP (0.5 mL) was added diisopropylethyl amine (0.50 mL, 2.9 mmol), and 8-oxa-3-azabicyclo[3.2.1]octane (0.17 g, 0.72 mmol). The resulting mixture was irradiated with microwaves (100° C.) for 1 h and loaded directly onto a silica column. Eluting the column with EtOAc/hexanes (0-100%) provided methyl 2-(8-oxa-3-azabicyclo[3.2.1]octan-3-yl)nicotinate as a clear oil (0.100 g, 42% yield). MS (ES) for $C_{13}H_{16}N_2O_3$: 249 (MH$^+$).

Step 1b: To a cooled (0° C.) solution of 2-(8-oxa-3-azabicyclo[3.2.1]octan-3-yl)nicotinate (0.10 g, 0.40 mmol) in THF (5 mL) was added a solution of lithium aluminum hydride (1.2 mL, 1M in THF). The reaction mixture was stirred for 1 h and then 20 µL of H$_2$O was added followed by 20 µL of 15% NaOH (aq) and then 60 µL of additional H$_2$O. The slurry was stirred for 1 h, filtered and the resulting residue was washed with ether. The combined organic layers were dried over MgSO$_4$ and concentrated in vacuo to yield (2-(8-oxa-3-azabicyclo[3.2.1]octan-3-yl)pyridin-3-yl)methanol (0.070 g, 79% yield). MS (ES) for $C_{12}H_{16}N_2O_2$: 221 (MH$^+$).

Step 2: To a cooled (0° C.) solution of (2-(8-oxa-3-azabicyclo[3.2.1]octan-3-yl)pyridin-3-yl)methanol (0.070 g, 0.32 mmol) in dichloromethane was added SOCl$_2$ (0.23 mL, 3.2 mmol) and the reaction mixture was allowed to warm to ambient temperature. After 1 h, the reaction mixture was concentrated and azeotroped with toluene three times to provide 3-(3-(chloromethyl)pyridin-2-yl)-8-oxa-3-azabicyclo[3.2.1]octane (0.075 g, 98%) as a clear oil. MS (ES) for $C_{12}H_{15}ClN_2O$: 239 (MH$^+$).

Step 3: To a solution of provide 3-(3-(chloromethyl)pyridin-2-yl)-8-oxa-3-azabicyclo[3.2.1]octane (0.080 g, 0.35 mmol) and 5-hydroxy-2,2-dimethyl-4H-benzo[d][1,3]dioxin-4-one (0.061 g, 0.31 mmol) in DMF was added cesium carbonate (0.307 g, 0.94 mmol) and the reaction mixture was heated (60° C.). After 30 minutes, the reaction mixture was partitioned between EtOAc and saturated aqueous sodium bicarbonate and the aqueous layer was extracted two times with EtOAc. Combined organic layers were washed with brine, dried over MGSO$_4$ and concentrated in vacuo. Purification by silica gel chromatography yielded 5-((2-(8-oxa-3-azabicyclo[3.2.1]octan-3-yl)pyridin-3-yl)methoxy)-2,2-dimethyl-4H-benzo[d][1,3]dioxin-4-one (112 mg, 90% yield). MS (ES) for $C_{22}H_{24}N_2O_5$: 397 (MH$^+$).

Step 4: To a cooled (−78° C.) solution of 5-((2-(3-oxa-8-azabicyclo[3.2.1]octan-8-yl)pyridin-3-yl)methoxy)-2,2-dimethyl-4H-benzo[d][1,3]dioxin-4-one (0.11 g, 0.28 mmol) in CH$_2$Cl$_2$ was added DIBAL-H (0.85 mL, 1M in CH$_2$Cl$_2$) and reaction mixture was allowed to warm to ambient temperature over 3 hours. The reaction mixture was then cooled (−78° C.) and MeOH was added followed by saturated potassium sodium tartrate solution (300 µL). This mixture was stirred for 2 hours at ambient temperature and filtered over Celite. The resulting solution was partitioned between EtOAc and saturated aqueous NaHCO$_3$ and washed two times with EtOAc. The combined organic layers were washed with brine, dried over MgSO$_4$ and concentrated in vacuo. Purification by preparatory HPLC resulted in 2-((2-(8-oxa-3-azabicyclo[3.2.1]octan-3-yl)pyridin-3-yl)methoxy)-6-hydroxybenzaldehyde (0.025 g, 25% yield). $^1$H NMR (400 MHz, Chloroform-d) δ 11.95 (s, 1H), 10.39 (d, J=0.6 Hz, 1H), 8.32 (dd, J=4.8, 1.9 Hz, 1H), 7.74 (dd, J=8.0, 2.1 Hz, 1H), 7.40 (t, J=8.4 Hz, 1H), 7.00 (dd, J=7.5, 4.8 Hz, 1H), 6.56 (d, J=8.5 Hz, 1H), 6.39 (d, J=8.3 Hz, 1H), 5.15 (s, 2H), 4.47-4.40 (m, 2H), 3.33 (dd, J=12.5, 2.0 Hz, 2H), 3.03 (dd, J=12.3, 1.4 Hz, 2H), 2.13-1.94 (m, 4H). MS (ES) for $C_{19}H_{20}N_2O_4$: 341 (MH$^+$).

GBT911

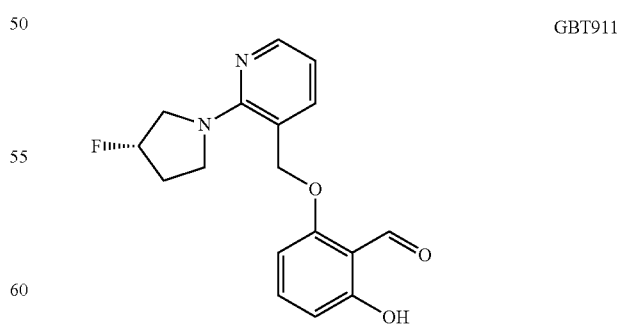

GBT911

GBT911—2-((2-(8-oxa-3-azabicyclo[3.2.1]octan-3-yl)pyridin-3-yl)methoxy)-6-hydroxybenzaldehyde. The compound was prepared from ethyl 2-fluoronicotinate and (S)-3-fluoropyrrolidine according to reaction scheme below.

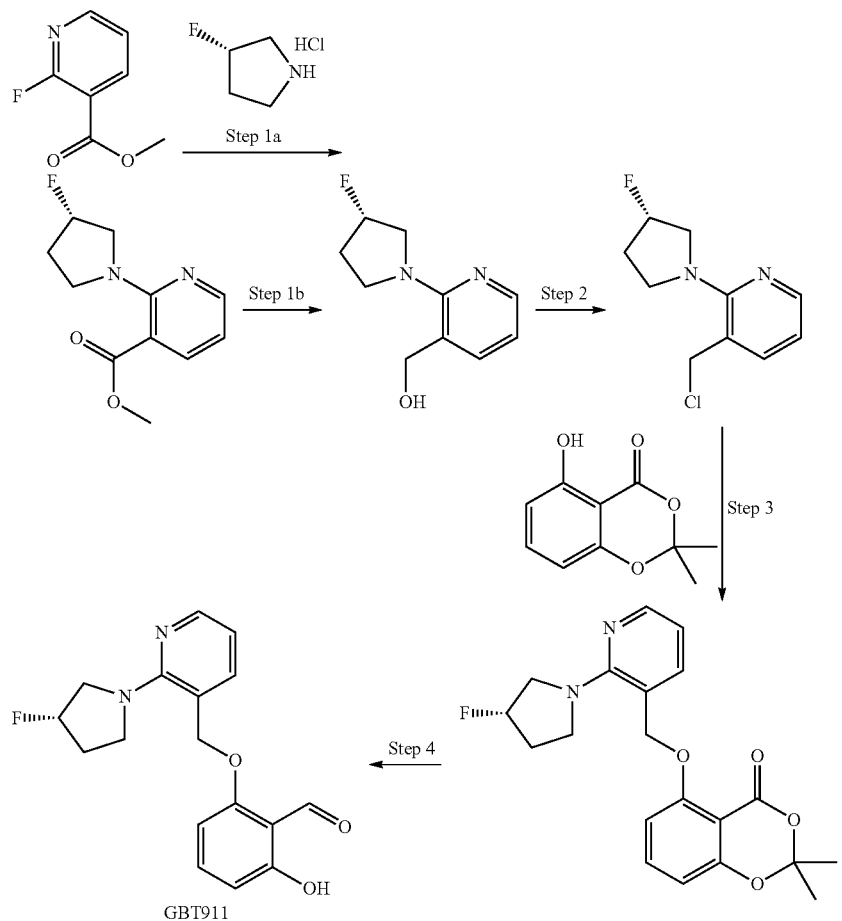

GBT911

Step 1a: To a solution of ethyl 2-fluoronicotinate (0.090 g, 0.58 mmol) in DMF (0.3 mL) was added diisopropylethyl amine (0.51 mL, 2.9 mmol), and (S)-3-fluoropyrrolidine (0.10 g, 1.2 mmol). The resulting mixture was irradiated with microwaves (100° C.) for 1 h and loaded directly onto a silica column. Eluting the column with EtOAc/hexanes (0-100%) provided (S)-ethyl 2-(3-fluoropyrrolidin-1-yl) nicotinate as a clear oil (0.100 g, 46% yield). MS (ES) for $C_{12}H_{15}FN_2O_2$: 225 (MH$^+$).

Step 1b: To a cooled (0° C.) solution of (S)-methyl 2-(3-fluoropyrrolidin-1-yl)nicotinate (0.20 g, 0.87 mmol) in THF (5 mL) was added a solution of lithium aluminum hydride (2.6 mL, 1M in THF). The reaction mixture was stirred for 1 h and then 20 μL of $H_2O$ was added followed by 20 μL of 15% NaOH (aq) and then 60 μL of additional $H_2O$. The slurry was stirred for 1 h, filtered and the resulting residue was washed with ether. The combined organic layers were dried over MgSO$_4$ and concentrated in vacuo. Purification by column chromotography (EtOAc/hexanes, 0-100%) provided (S)-(2-(3-fluoropyrrolidin-1-yl)pyridin-3-yl)methanol (0.165 g, 97% yield). MS (ES) for $C_{10}H_{13}FN_2O$: 197 (MH$^+$).

Step 2: To a cooled (0° C.) solution of (S)-(2-(3-fluoropyrrolidin-1-yl)pyridin-3-yl)methanol (0.081 g, 0.77 mmol) in dichloromethane was added SOCl$_2$ (0.92 g, 7.7 mmol) and the reaction mixture was allowed to warm to ambient temperature. After 1 h, the reaction mixture was concentrated and azeotroped with toluene to provide (S)-3-(chloromethyl)-2-(3-fluoropyrrolidin-1-yl)pyridine (0.180 g, 99%) as a clear oil. MS (ES) for $C_{10}H_{12}ClFN_2$: 215 (MH$^+$).

Step 3: To a solution of provide (S)-3-(chloromethyl)-2-(3-fluoropyrrolidin-1-yl)pyridine (0.085 g, 0.40 mmol) and 5-hydroxy-2,2-dimethyl-4H-benzo[d][1,3]dioxin-4-one (0.12 g, 0.59 mmol) in DMF was added cesium carbonate (0.39 g, 0.12 mmol) and the reaction mixture was heated (60° C.). After 30 minutes, the reaction mixture was partitioned between EtOAc and saturated aqueous sodium bicarbonate and the aqueous layer was extracted two times with EtOAc. Combined organic layers were washed with brine, dried over MGSO$_4$ and concentrated in vacuo. Purification by silica gel chromatography yielded (S)-5-((2-(3-fluoropyrrolidin-1-yl)pyridin-3-yl)methoxy)-2,2-dimethyl-4H-benzo[d][1,3]dioxin-4-one (120 mg, 81% yield). MS (ES) for $C_{20}H_{21}FN_2O_4$: 373 (MH$^+$).

Step 4: To a cooled (−78° C.) solution of (S)-5-((2-(3-fluoropyrrolidin-1-yl)pyridin-3-yl)methoxy)-2,2-dimethyl-4H-benzo[d][1,3]dioxin-4-one (0.085 g, 0.23 mmol) in CH$_2$Cl$_2$ was added DIBAL-H (0.68 mL, 1M in CH$_2$Cl$_2$) and reaction mixture was allowed to warm to ambient temperature over 3 hours. The reaction mixture was then cooled (−78° C.) and MeOH was added followed by saturated potassium sodium tartrate solution (300 μL). This mixture was stirred for 2 hours at ambient temperature and filtered over Celite. The resulting solution was partitioned between EtOAc and saturated aqueous NaHCO₃ and washed two times with EtOAc. The combined organic layers were washed with brine, dried over MgSO₄ and concentrated in vacuo. Purification by preparatory HPLC resulted in 2-((2-(8-oxa-3-azabicyclo[3.2.1]octan-3-yl)pyridin-3-yl)methoxy)-6-hydroxybenzaldehyde (0.020 g, 28% yield). ¹H NMR (400 MHz, Chloroform-d) δ 11.97 (s, 1H), 10.34 (s, 1H), 8.21 (dd, J=4.8, 1.9 Hz, 1H), 7.56 (ddd, J=7.4, 1.9, 0.5 Hz, 1H), 7.42 (t, J=8.4 Hz, 1H), 6.75 (dd, J=7.4, 4.8 Hz, 1H), 6.57 (d, J=8.0 Hz, 1H), 6.44 (d, J=9.0 Hz, 1H), 5.24 (dt, J=53.0, 3.9, 3.3 Hz, 1H), 5.16 (d, J=11.4 Hz, 1H), 5.05 (d, J=11.4 Hz, 1H), 3.97-3.60 (m, 4H), 2.37-1.96 (m, 2H). MS (ES) for C₁₇H₁₇FN₂O₃: 317 (MH⁺).

GBT001028

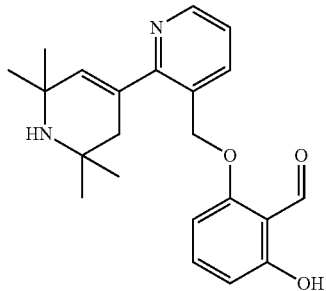 [SMILES: CC1(C)C=C(c2ncccc2COc2cccc(O)c2C=O)CC(C)(C)N1]

GBT1028—2-hydroxy-6-((2',2',6',6'-tetramethyl-1',2',3',6'-tetrahydro-[2,4'-bipyridin]-3-yl)methoxy)benzaldehyde. The compound was prepared by Suzuki coupling of 2,2,6,6-tetramethyl-4-(4,4,5,5-tetramethyl-1,3,2-dioxaborolan-2-yl)-1,2,3,6-tetrahydropyridine and 2-((2-bromopyridin-3-yl)methoxy)-6-(methoxymethoxy)benzaldehyde according to scheme 4, reaction step 2; the MOM ether protecting group was removed by treating with conc HCl (2eq) in THF. The product HCl salt was obtained as brown solid after silica gel chromatography. ¹H NMR (400 MHz, DMSO-d₆) δ 11.70 (s, 1H), 10.30 (s, 1H), 9.21 (s, 2H), 8.62 (dd, J=4.9, 1.6 Hz, 1H), 8.24-8.16 (m, 1H), 7.58-7.46 (m, 2H), 6.67 (d, J=8.3 Hz, 1H), 6.56 (d, J=8.4 Hz, 1H), 5.94 (d, J=1.8 Hz, 1H), 5.26 (s, 2H), 3.66-3.54 (m, 2H), 1.56-1.37 (m, 12H); MS (ES, m/z) 367.38 [M+1]+.

GBT1045

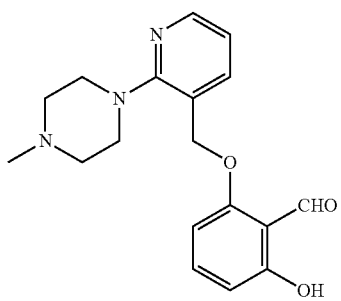 [SMILES: CN1CCN(c2ncccc2COc2cccc(O)c2C=O)CC1]

GBT1045-2-hydroxy-6-((2-(4-methylpiperazin-1-yl)pyridin-3-yl)methoxy)benzaldehyde. The compound was prepared from methyl 2-chloronicotinate and methylpiperazine according to scheme 5, reaction steps 1 and 2.

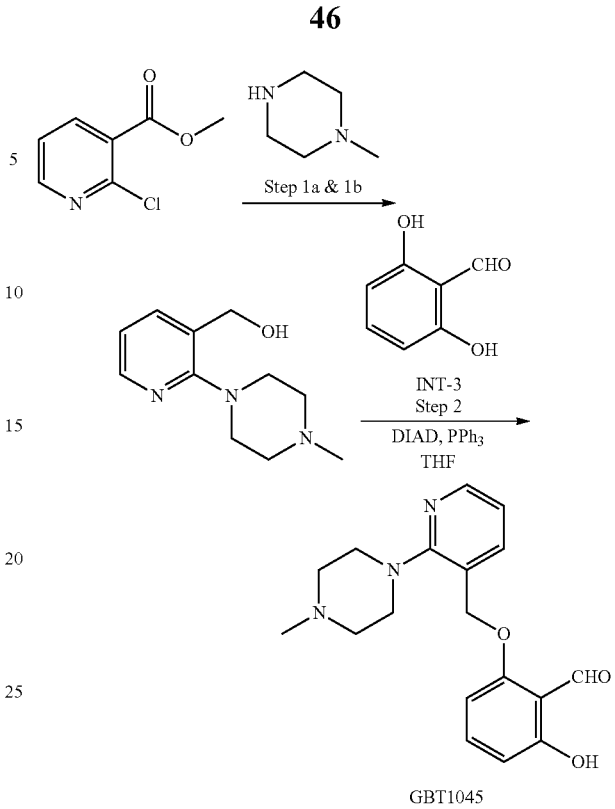

Step 1a: Into a 100-mL round-bottom flask, was placed a solution of methyl 2-chloropyridine-3-carboxylate (2.0 g, 11.66 mmol, 1.00 equiv) in N,N-dimethylformamide (40 mL). 1-methylpiperazine (1.75 g, 17.47 mmol, 1.50 equiv), potassium carbonate (3.30 g, 23.88 mmol, 2.00 equiv), 18-crown-6 (200 mg, 0.06 equiv) were added to the reaction. The resulting solution was stirred overnight at 100° C. The reaction mixture was cooled to room temperature. The resulting solution was diluted with 30 mL of H₂O, and then it was extracted with 5×30 mL of ethyl acetate. The combined organic layers were concentrated under vacuum. The residue was applied onto a silica gel column with dichloromethane/methanol (10:1) as eluent. This resulted in 2.7 g (98%) of methyl 2-(4-methylpiperazin-1-yl)pyridine-3-carboxylate as a yellow oil.

Step 1b: Into a 100-mL round-bottom flask, was placed a solution of methyl 2-(4-methylpiperazin-1-yl)pyridine-3-carboxylate (1.3 g, 5.53 mmol, 1.00 equiv) in tetrahydrofuran (40 mL). This was followed by the addition of AlLiH₄ (315 mg, 8.30 mmol, 1.50 equiv) at 0° C. The resulting solution was stirred for 5 h at 0° C., and then it was quenched by the addition of 0.5 mL of water, 1.5 ml of NaOH (15%) and 0.5 ml of water. The solids were filtered out. The resulting mixture was concentrated under vacuum. The residue was applied onto a silica gel column with dichloromethane/methanol (1:1) as eluent. This resulted in 500 mg (44%) of [2-(4-methylpiperazin-1-yl)pyridin-3-yl]methanol as a yellow solid.

Step 2: Into a 50-mL round-bottom flask, was placed a solution of [2-(4-methylpiperazin-1-yl)pyridin-3-yl]methanol (200 mg, 0.96 mmol, 1.00 equiv) in tetrahydrofuran (20 mL). 2,6-Dihydroxybenzaldehyde (200 mg, 1.45 mmol, 1.50 equiv) and PPh₃ (380 mg, 1.45 mmol, 1.50 equiv) were added to the reaction. This was followed by the addition of DIAD (293 mg, 1.45 mmol, 1.50 equiv) at 0° C. The resulting solution was stirred overnight at room temperature, and then it was concentrated under vacuum. The crude product (200 mg) was purified by Prep-HPLC with the following conditions (Prep-HPLC-010): Column, SunFire Prep C18 OBD Column, 5 um, 19*150 mm; mobile phase, water with 0.05% TFA and MeCN (25.0% MeCN up to 42.0% in 13 min, up to 95.0% in 2 min, down to 25.0% in 2 min); Detector, Waters2545 UvDector 254&220 nm. This resulted in 67.9 mg (21%) of 2-hydroxy-6-[[2-(4-methyl-piperazin-1-yl)pyridin-3-yl]methoxy]benzaldehyde as a yellow oil; $^1$HNMR (400 MHz, CDCl$_3$, ppm): 11.98 (s, 1H), 10.43 (s, 6H), 8.35 (m, 1H), 7.77 (d, J=5.7 Hz, 1H), 7.42 (m, 1H), 7.03 (m, 1H), 6.58 (d, J=6.3 Hz, 1H), 6.43 (d, J=6.0 Hz, 1H), 5.18 (d, J=7.8 Hz, 2H), 3.26 (m, 4H), 2.64 (s, 4H), 2.40 (s, 3H) 1.42-2.09 (m, 8H); MS (ES, m/z): 328 [M+1]$^+$.

GBT1249

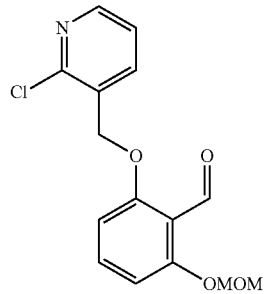

GBT1249—2-((2-chloropyridin-3-yl)methoxy)-6-(methoxymethoxy)benzaldehyde. The compound was prepared by O-alkylation of 2-hydroxy-6-(methoxymethoxy)benzaldehyde and 2-chloro-3-(chloromethyl)pyridine. The product as white solid was obtained after flash column purification. $^1$HNMR (400 MHz, CDCl$_3$, ppm): 10.65 (s, 1H), 8.37 (d, J=5.7 Hz, 1H), 7.49 (t, J=6.3 Hz, 1H), 7.39 (t, J=4.5 Hz, 1H), 7.28 (s, 1H), 6.90 (d, J=6.3 Hz, 1H), 6.75 (d, J=6.3 Hz, 1H), 5.32 (s, 2H), 5.21 (s, 2H), 3.54 (s, 3H); MS (ES, m/z): 308[M+1]$^+$

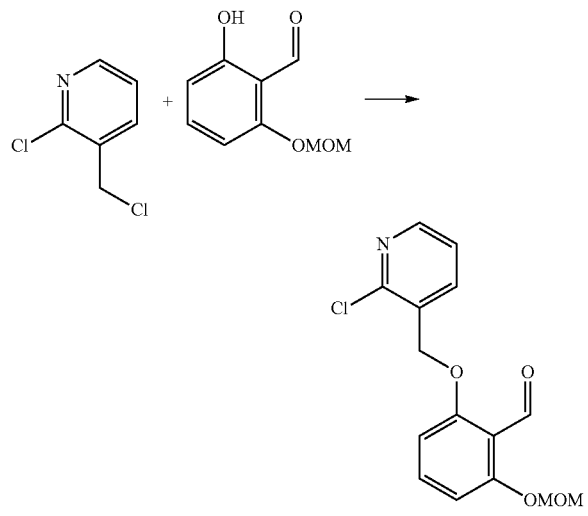

GBT001046

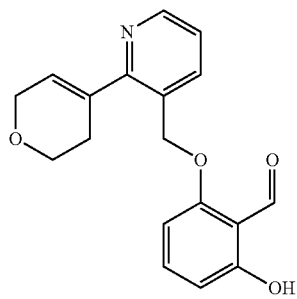 [SMILES: O=Cc1c(O)cccc1OCc1cccnc1C1=CCOCC1]

GBT1046—2-((2-(3,6-dihydro-2H-pyran-4-yl)pyridin-3-yl)methoxy)-6-hydroxybenzaldehyde.

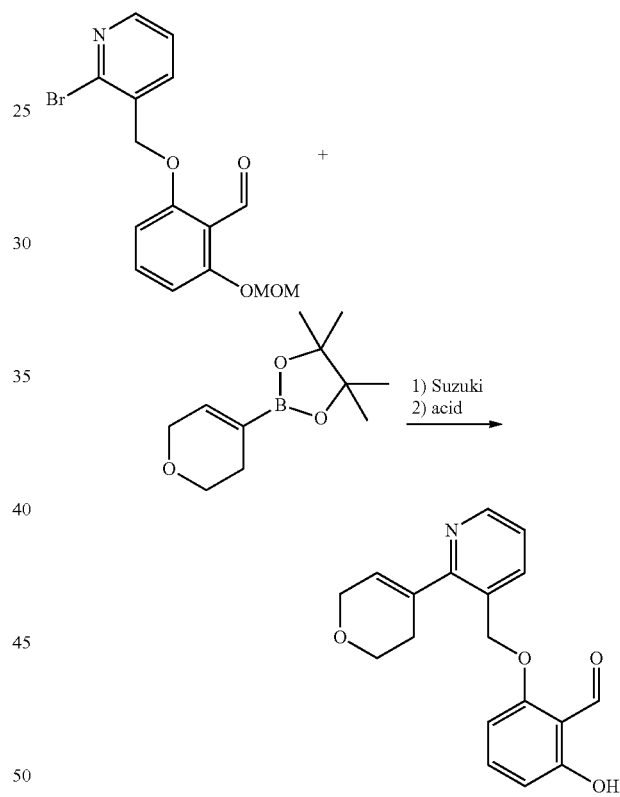

The compound was prepared by Suzuki coupling of 2-(3,6-dihydro-2H-pyran-4-yl)-4,4,5,5-tetramethyl-1,3,2-dioxaborolane and 2-((2-bromopyridin-3-yl)methoxy)-6-(methoxymethoxy)benzaldehyde according to scheme 4, reaction step 2; the MOM ether protecting group was removed by treating with conc HCl (2eq) in THF. The product was obtained as light brown solid after silica gel chromatography. $^1$H NMR (400 MHz, Chloroform-d) d 11.93 (d, J=0.6 Hz, 1H), 10.37 (s, 1H), 8.84 (s, 1H), 8.56 (d, J=7.2 Hz, 1H), 7.89 (s, 1H), 7.46 (t, J=8.3 Hz, 1H), 6.67 (d, J=8.5 Hz, 1H), 6.36 (d, J=7.6 Hz, 2H), 5.29 (s, 2H), 4.43 (s, 2H), 4.08 (t, J=4.5 Hz, 2H), 2.80 (s, 2H); MS (ES, m/z) 312.33 [M+1]$^+$.

GBT1063

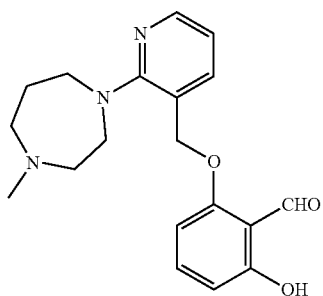 [SMILES: CN1CCCN(c2ncccc2COc2cccc(O)c2C=O)CC1]

GBT1063—2-hydroxy-6-((2-(4-methyl-1,4-diazepan-1-yl)pyridin-3-yl)methoxy)benzaldehyde. The compound was prepared from methyl 2-chloronicotinate and 1-methyl-1,4-diazepane according to scheme 5, reaction steps 1 and 2.

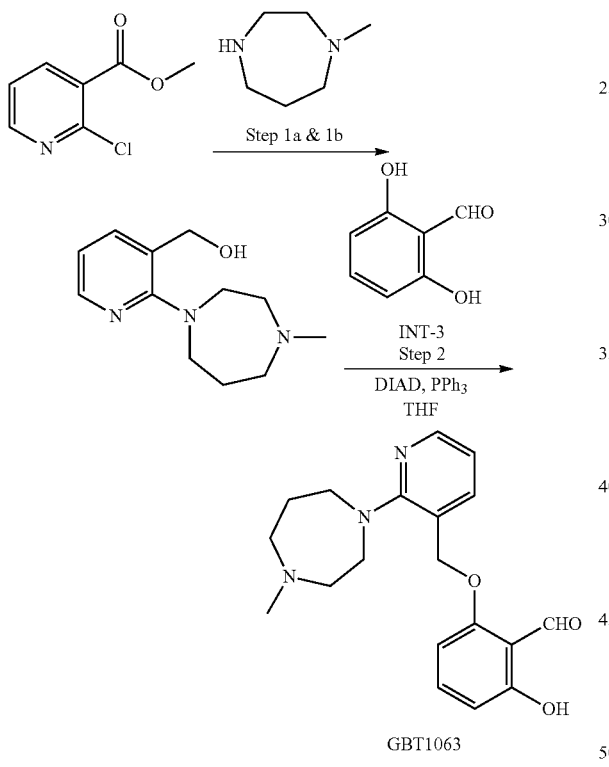

Step 1a: Into a 100-mL round-bottom flask, was placed a solution of methyl 2-chloropyridine-3-carboxylate (2.0 g, 11.66 mmol, 1.00 equiv) in N,N-dimethylformamide (40 mL). 1-methyl-1,4-diazepane (2.0 g, 17.51 mmol, 1.50 equiv), potassium carbonate (3.3 g, 23.88 mmol, 2.00 equiv), and 18-crown-6 (200 mg, 0.06 equiv) were added to the reaction. The resulting solution was stirred overnight at 100° C. The reaction mixture was cooled to room temperature, and then it was diluted with 40 mL of H$_2$O. The resulting solution was extracted with 5×30 mL of ethyl acetate and the combined organic layers were concentrated under vacuum. The residue was applied onto a silica gel column with dichloromethane/methanol (10:1) as eluent. This resulted in 2.65 g (91%) of methyl 2-(4-methyl-1,4-diazepan-1-yl)pyridine-3-carboxylate as a yellow oil.

Step 1b: Into a 100-mL round-bottom flask, was placed a solution of methyl 2-(4-methyl-1,4-diazepan-1-yl)pyridine-3-carboxylate (1.2 g, 4.81 mmol, 1.00 equiv) in tetrahydrofuran (40 mL). This was followed by the addition of LiAlH$_4$ (500 mg, 13.18 mmol, 2.00 equiv) at 0° C. The resulting solution was stirred for 2 h at room temperature. The reaction was then quenched by the addition of 0.5 mL of water, 1.5 mL of 15% NaOH, 0.5 mL of H$_2$O. The solids were filtered out. The resulting mixture was concentrated under vacuum. The residue was applied onto a silica gel column with dichloromethane/methanol (3:1) as eluent. This resulted in 800 mg (75%) of [2-(4-methyl-1,4-diazepan-1-yl)pyridin-3-yl]methanol as a yellow oil.

Step 2: Into a 50-mL round-bottom flask, was placed a solution of [2-(4-methyl-1,4-diazepan-1-yl)pyridin-3-yl]methanol (300 mg, 1.36 mmol, 1.00 equiv) in tetrahydrofuran (25 mL). 2,6-Dihydroxybenzaldehyde (280 mg, 2.03 mmol, 1.50 equiv) and PPh$_3$ (532 mg, 2.03 mmol, 1.50 equiv) were added to the reaction. This was followed by the addition of DIAD (410 mg, 2.03 mmol, 1.50 equiv) at 0° C. The resulting solution was stirred overnight at room temperature, and then it was concentrated under vacuum. The crude product (300 mg) was purified by Prep-HPLC with the following conditions (Prep-HPLC-010): Column, Gemini-NX 150*21.20 mm C18 AXIA Packed, 5 um 110 A; mobile phase, water with 0.05% TFA and MeCN (10.0% MeCN up to 50.0% in 5 min); Detector, nm. This resulted in 159.5 mg (34%) of 2-hydroxy-6-[[2-(4-methyl-1,4-diazepan-1-yl)pyridin-3-yl]methoxy]benzaldehyde as a yellow oil; $^1$HNMR (400 MHz, DMSO+D$_2$O, ppm): 10.29 (s, 1H), 8.19 (d, J=2.7 Hz, 1H), 7.95 (d, J=5.4 Hz, 1H), 7.52 (m, 1H), 7.08 (m, 1H), 6.66 (d, J=6.3 Hz, 1H), 6.57 (d, J=0.9 Hz, 1H), 5.21 (s, 2H), 3.74 (s, 2H), 3.45 (m, 6H), 2.84 (s, 3H), 2.11 (d, J=3.9 Hz, 2H); (ES, m/z): 342 [M+1]$^+$.

GBT001121

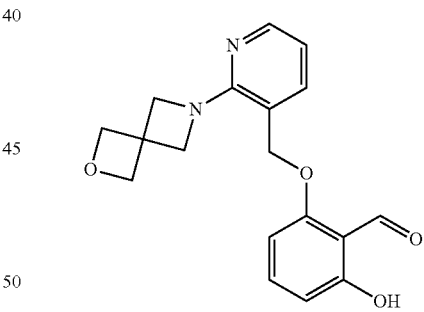

GBT1121—2-((2-(2-oxa-6-azaspiro[3.3]heptan-6-yl)pyridin-3-yl)methoxy)-6-hydroxybenzaldehyde. The compound was prepared from methyl 2-fluoronicotinate and 2-oxa-6-azaspiro[3.3]heptane according to scheme 5, reaction steps 1 and 2.

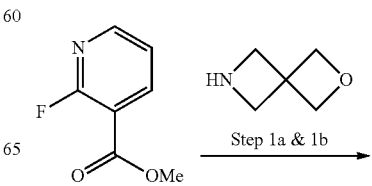

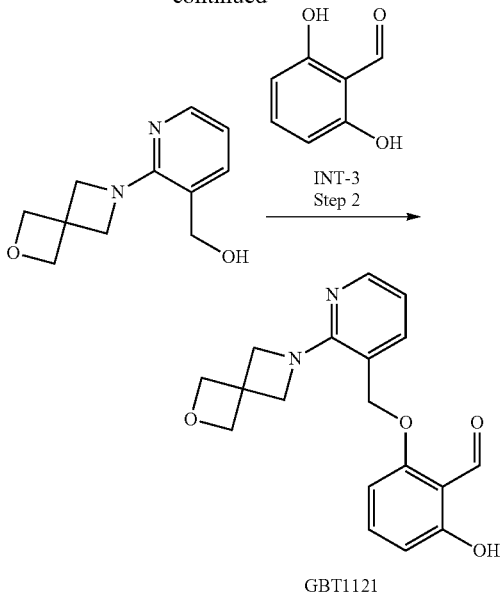

GBT1121

Step 1a: Methyl 2-fluoronicotinate (0.3 g, 1.93 mmol) and 2-oxa-6-azaspiro[3.3]heptane oxalate (0.55 g, 2.9 mmol) were combined with DMF (3 ml). N,N-diisopropylethylamine (2 ml, 11.6 mmol) was added and the mixture was heated in a microwave reactor (120° C., 1 h). Ethyl acetate (100 ml) and water (50 ml) were added to the cooled solution and the phases were separated. The aqueous phase was extracted with ethyl acetate (2×50 ml). The combined organic phases were washed with water (30 ml) and a saturated aqueous sodium chloride solution (30 ml), and dried over sodium sulfate. After evaporation, the residue was purified by silica gel chromatography (5-80% ethyl acetate/hexanes) to give 0.27 g (59%) of methyl 2-(2-oxa-6-azaspiro[3.3]heptan-6-yl)nicotinate as a white solid. MS (ESI) m/z 235 [M+H]$^+$.

Step 1b: Methyl 2-(2-oxa-6-azaspiro[3.3]heptan-6-yl)nicotinate (0.26 g, 1.1 mmol) was dissolved in THF (5 ml) and stirred in an ice bath. Lithium aluminum hydride (2.2 ml of a 1M THF solution) was added dropwise. The reaction was stirred to 25° C. over 2 h. Water (0.084 ml) was carefully added followed by 15% aqueous sodium hydroxide solution (0.084 ml) and water (0.25 ml). The mixture was stirred for 30 m then filtered, rinsed with THF (10 ml) and the solvent evaporated to give 226 mg (98%) of (2-(2-oxa-6-azaspiro[3.3]heptan-6-yl)pyridin-3-yl)methanol which was used directly in the next step. MS (ESI) m/z 207 [M+H]$^+$.

Step 2: 2-(2-Oxa-6-azaspiro[3.3]heptan-6-yl)pyridin-3-yl)methanol (0.12 g, 0.582 mmol) 2,6-dihydroxybenzaldehyde (96 mg, 0.7 mmol) and triphenylphosphine-polystyrene resin (0.63 g, 0.76 mmol) were combined with THF (3 ml), and stirred in an ice bath. Diisopropylazodicarboxylate (0.15 ml, 0.76 mmol) was added dropwise and the reaction was stirred to 25° C. over 16 h. The reaction was filtered, rinsed with THF (10 ml) and evaporated. The resulting residue was purified by silica gel chromatography (0-75% ethyl acetate/dichloromethane) to give 31 mg (16%) of 2-((2-(2-oxa-6-azaspiro[3.3]heptan-6-yl)pyridin-3-yl)methoxy)-6-hydroxybenzaldehyde as a white solid after lyophilization from acetonitrile/water. $^1$H NMR (400 MHz, CDCl$_3$) δ 11.97 (s, 1H), 10.36 (s, 1H), 8.21 (dd, J=1.65, 4.92 Hz, 1H), 7.51 (dd, J=1.68, 7.37 Hz, 1H), 7.44 (t, J=8.38 Hz, 1H), 6.76 (dd, J=4.95, 7.34 Hz, 1H), 6.60 (d, J=8.49 Hz, 1H), 6.42 (d, J=8.28 Hz, 1H), 4.96 (s, 2H), 4.81 (s, 4H), 4.27 (s, 4H). MS (ESI) m/z 327 [M+H]+.

GBT001122

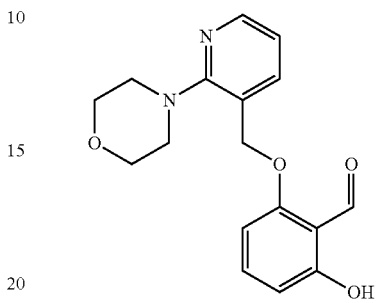

GBT1122—2-Hydroxy-6-((2-morpholinopyridin-3-yl)methoxy)benzaldehyde. The compound was prepared from ethyl 2-fluoronicotinate and morpholine according to a modified scheme 5, reaction steps 1, 3 and 4.

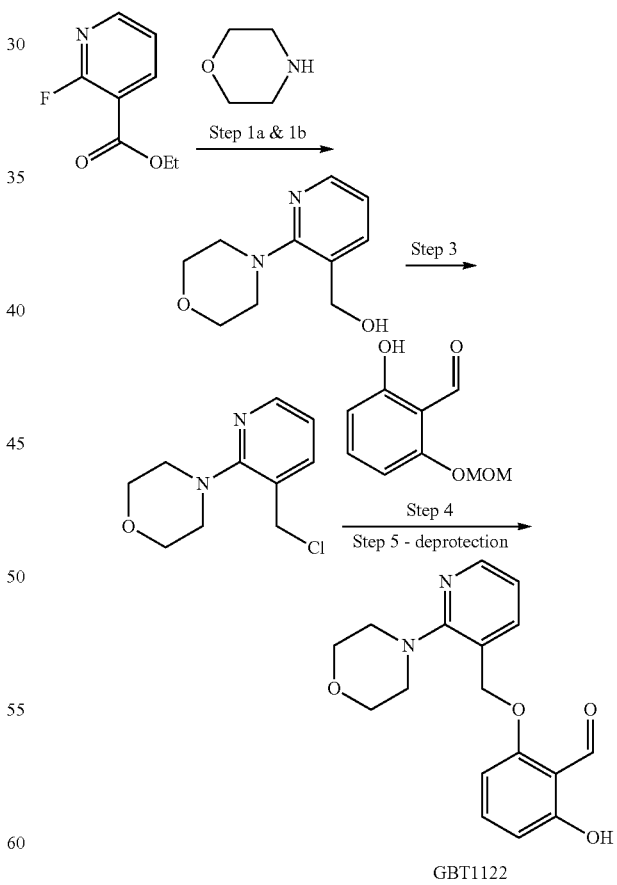

GBT1122

Step 1a: To a solution of ethyl 2-fluoronicotinate (0.40 g, 2.6 mmol) in DMF (0.3 mL) was added diisopropylethyl amine (1.8 mL, 10 mmol), and morpholine (0.45 g, 5.2 mmol). The resulting mixture was irradiated with microwaves (100° C.) for 1 h and loaded directly onto a silica column. Eluting the column with EtOAc/hexanes (0-100%) Methyl 2-morpholinonicotinate as a clear oil (0.36 g, 62% yield). MS (ES) for $C_{12}H_{16}N_2O_3$: 237 (MH$^+$).

Step 1b: To a cooled (0° C.) solution of Methyl 2-morpholinonicotinate (0.36 g, 1.6 mmol) in THF (5 mL) was added a solution of lithium aluminum hydride (4.9 mL, 1M in THF). The reaction mixture was stirred for 1 h and then 180 μL of H2O was added followed by 180 μL of 15% NaOH (aq) and then 540 μL of additional water. The slurry was stirred for 1 h and filtered and the resulting residue was washed with ether. The combined organic layers were dried over MgSO$_4$ and concentrated in vacuo. Purification by column chromotography (EtOAc/hexanes, 0-100%) provided (2-morpholinopyridin-3-yl)methanol (0.224 g, 71% yield). MS (ES) for $C_{10}H_{14}N_2O_2$: 195 (MH$^+$).

Step 3: To a cooled (0° C.) solution of provided (2-morpholinopyridin-3-yl)methanol (0.100 g, 0.51 mmol) in dichloromethane was added SOCl$_2$ (0.50 mL, 6.9 mmol) and the reaction mixture was allowed to warm to ambient temperature. After 1 h, the reaction mixture was concentrated and azeotroped with toluene to provide 4-(3-(chloromethyl)pyridin-2-yl)morpholine (0.11 g, 96%) as a clear oil. MS (ES) for $C_{10}H_{13}ClN_2O$: 213 (MH$^+$).

Step 4: To a solution of 4-(3-(chloromethyl)pyridin-2-yl) morpholine (0.11 g, 0.50 mmol) and 2-hydroxy-6-(methoxymethoxy)benzaldehyde (0.09 g, 0.50 mmol) in DMF was added potassium carbonate (0.210 g, 1.5 mmol) and the reaction mixture was heated (60° C.). After 30 minutes, the reaction mixture was partitioned between EtOAc and saturated NaHCO$_3$ and the aqueous layer was extracted twice with EtOAc. The combined organic layers were washed with brine, dried over MgSO$_4$ and concentrated in vacuo to yield 2-(methoxymethoxy)-6-((2-morpholinopyridin-3-yl)methoxy)benzaldehyde (0.145 mg, 80% yield) as a white powder. MS (ES) for $C_{19}H_{22}N_2O_5$: 359 (MH$^+$).

Step 5: To a solution of 2-(methoxymethoxy)-6-((2-morpholinopyridin-3-yl)methoxy)benzaldehyde (0.120 g, 0.33 mmol) in THF (5 mL) was added concentrated HCl (0.5 mL, 6 mmol). After stirring at ambient temperature for 3 hours, the mixture was partitioned between EtOAc and saturated aqueous NaHCO$_3$ and the aqueous phase was extracted twice with EtOAc. The combined organic layers were washed with brine, dried over MgSO$_4$ and concentrated in vacuo. Purification, reaction silica gel chromatography provided 2-hydroxy-6-((2-morpholinopyridin-3-yl)methoxy) benzaldehyde (0.074 g, 0.24 mmol) as a white powder. $^1$H NMR (400 MHz, Chloroform-d) δ 11.95 (s, 1H), 10.40 (s, 1H), 8.34 (dd, J=4.8, 1.9 Hz, 1H), 7.77 (dd, J=7.5, 1.7 Hz, 1H), 7.40 (t, J=8.4 Hz, 1H), 7.04 (dd, J=7.5, 4.9 Hz, 1H), 6.56 (d, J=8.5 Hz, 1H), 6.40 (d, J=8.3 Hz, 1H), 5.15 (s, 2H), 3.90-3.83 (m, 3H), 3.22-3.15 (m, 4H). MS (ES) for $C_{17}H_{18}N_2O_4$: 315 (MH$^+$).

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

The invention claimed is:

1. A compound of formula (II):

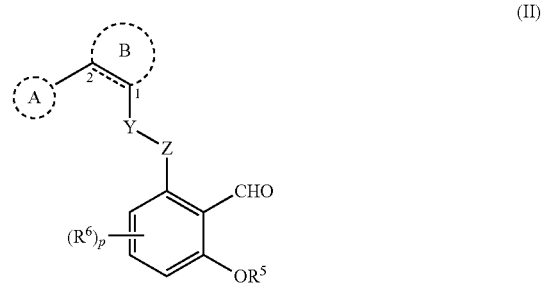

or a tautomer thereof, or a pharmaceutically acceptable salt of each thereof, wherein ring A is a 4-10 membered heterocycle containing up to 5 ring heteroatoms, wherein each heteroatom is independently selected from the group consisting of O, N, S, and oxidized forms of N and S, the heterocycle is saturated or contains one double bond, and the heterocycle is optionally substituted with 1, 2, 3, 4, or 5 substituents independently selected from halo, $C_1$-$C_6$ alkyl, and COOR$^{16}$, wherein R$^{16}$ is hydrogen or $C_1$-$C_6$ alkyl;

ring B is a phenyl or 5 or 6 membered heteroaryl having 1-3 nitrogen atoms, or oxidized versions thereof, wherein the phenyl or heteroaryl is optionally substituted with 1-3 substituents independently selected from the group consisting of halo, $C_1$-$C_6$ alkyl, COR$^{15}$, and COOR$^{15}$;

wherein R$^{15}$ is $C_1$-$C_6$ alkyl optionally substituted with halo;

⚋ is a single or a double bond;

each Y and Z is independently CR$^{10}$R$^{11}$, O, S, SO, or SO$_2$; each R$^{10}$ and R$^{11}$ independently is hydrogen or $C_1$-C3 alkyl optionally substituted with halo, OH, or $C_1$-$C_6$ alkoxy, or CR$^{10}$R$^{11}$ is C═O; provided that if one of Y and Z is O, S, SO, or SO$_2$, then the other is not C═O, and provided that Y and Z are not both heteroatoms or oxidized forms thereof;

R$^5$ is hydrogen or $C_1$-$C_6$ alkyl, wherein the C1-$C_6$ alkyl is optionally substituted with 1-5 halo;

R$^6$ is halo, $C_1$-$C_6$ alkyl, $C_1$-$C_6$ alkoxy, $C_1$-$C_6$ alkylthio, $C_1$-$C_6$ alkyl-S(O)—, or $C_1$-$C_6$ alkyl-S(O)$_2$—, wherein the $C_1$-$C_6$ alkyl is optionally substituted with 1-5 halo; and p is 0, 1, 2, or 3.

2. The compound of claim 1, or a tautomer thereof, or a pharmaceutically acceptable salt of each thereof, wherein p is 0.

3. The compound of claim 1, or a tautomer thereof, or a pharmaceutically acceptable salt of each thereof, wherein R$^6$ is halo; and p is 1.

4. A compound of Formula (IIA):

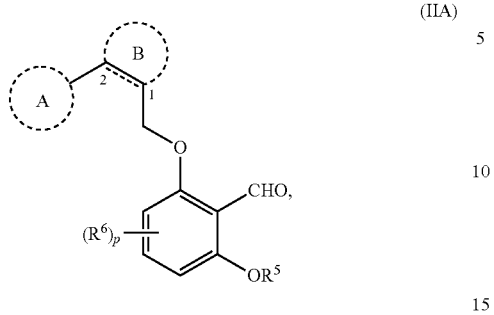

or a tautomer thereof, or a pharmaceutically acceptable salt of each thereof,
wherein
ring A is a 4-10 membered heterocycle containing up to 5 ring heteroatoms, wherein each heteroatom is independently selected from the group consisting of O, N, and S, the heterocycle is saturated or contains one double bond, and the heterocycle is optionally substituted with 1, 2, 3, 4, or 5 substituents independently selected from halo, $C_1$-$C_6$ alkyl, and $COOR^{16}$, wherein $R^{16}$ is hydrogen or $C_1$-$C_6$ alkyl;
ring B is phenyl or 5 or 6 membered heteroaryl having 1-3 nitrogen atoms, wherein the phenyl or heteroaryl is optionally substituted with 1-3 substituents independently selected from the group consisting of halo, $C_1$-$C_6$ alkyl, $COR^{15}$, and $COOR^{15}$; wherein $R^{15}$ is $C_1$-$C_6$ alkyl optionally substituted with halo;
⫽ is a single or a double bond;
$R^5$ is hydrogen or $C_1$-$C_6$ alkyl, wherein the $C_1$-$C_6$ alkyl is optionally substituted with 1-5 halo;
$R^6$ is halo, $C_1$-$C_6$ alkyl, $C_1$-$C_6$ alkoxy, $C_1$-$C_6$ alkylthio, $C_1$-$C_6$ alkyl-S(O)—, or $C_1$-$C_6$ alkyl-S(O)$_2$—,
wherein the $C_1$-$C_6$ alkyl is optionally substituted with 1-5 halo; and
p is 0, 1, 2, or 3.

5. The compound of claim 4, or a tautomer thereof, or a pharmaceutically acceptable salt of each thereof, wherein ring A is optionally substituted with 1, 2, or 3 substituents independently selected from the group consisting of halo and $C_1$-$C_6$ alkyl.

6. The compound of claim 4, or a tautomer thereof, or a pharmaceutically acceptable salt of each thereof, wherein ring B is pyridinyl optionally substituted with one substituent selected from the group consisting of halo, $C_1$-$C_6$ alkyl, $COR^{15}$, and $COOR^{15}$; wherein $R^{15}$ is $C_1$-$C_6$ alkyl.

7. The compound of claim 1, wherein the compound is selected from the group consisting of

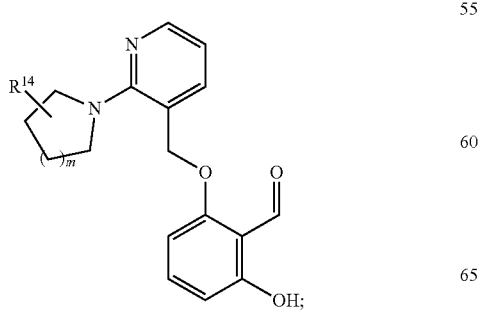

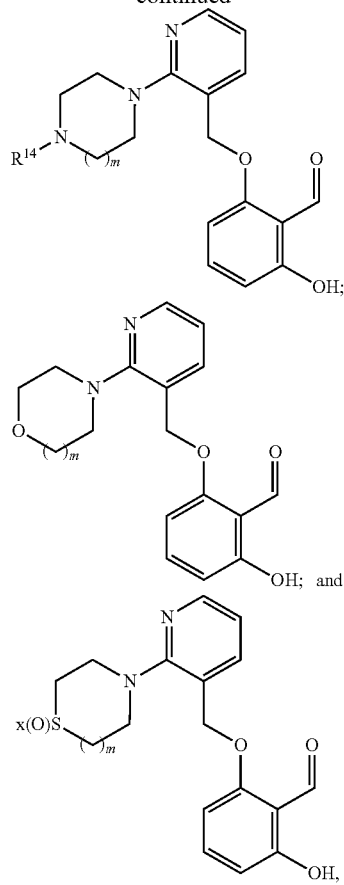

or an N oxide thereof, or a tautomer thereof, or a pharmaceutically acceptable salt of each thereof, wherein
$R^{14}$ is $C_1$-$C_6$ alkyl;
x is 0, 1, or 2; and
m is 0, 1, or 2.

8. A compound selected from the group consisting of:

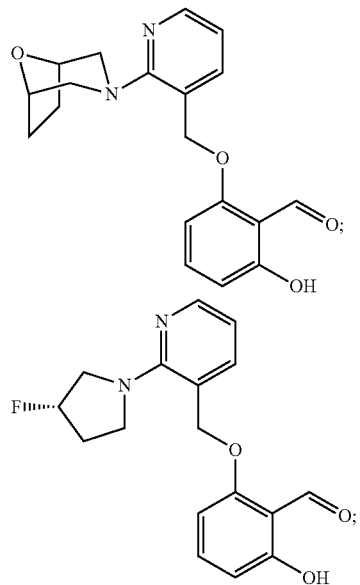

-continued

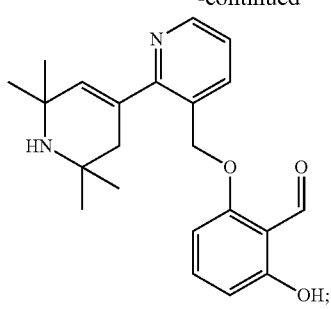

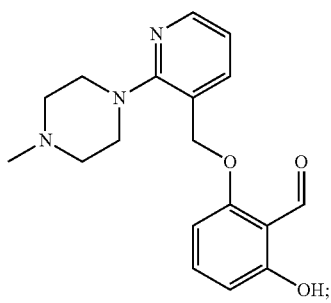

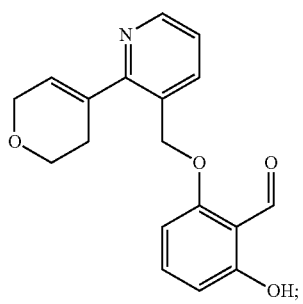

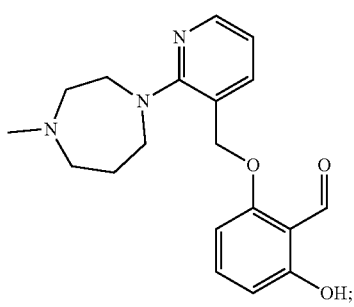

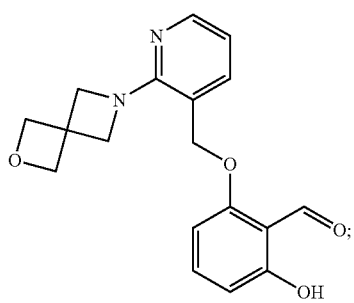

-continued

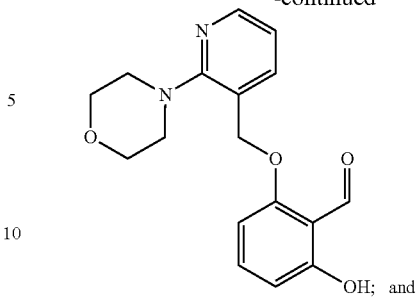

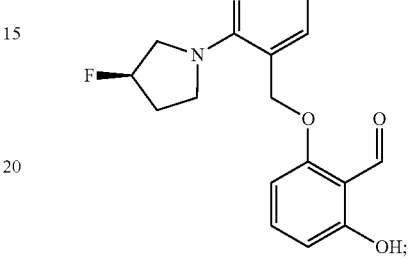

or a tautomer thereof, or a pharmaceutically acceptable salt of each thereof.

9. A pharmaceutical composition comprising a compound of claim 1, or a tautomer thereof, or a pharmaceutically acceptable salt of each thereof, and at least one pharmaceutically acceptable excipient.

10. A method for increasing oxygen affinity of hemoglobin S in a subject, the method comprising administering to a subject in need thereof a compound of claim 1, or a tautomer thereof, or a pharmaceutically acceptable salt of each thereof.

11. A method for treating sickle cell disease, the method comprising administering to a subject in need thereof a compound of claim 1, or a tautomer thereof, or a pharmaceutically acceptable salt of each thereof.

12. The compound of claim 1, or a tautomer thereof, or a pharmaceutically acceptable salt of each thereof, wherein ring A is optionally substituted with 1, 2, 3, or 4 substituents independently selected from the group consisting of halo and $C_1$-$C_6$ alkyl.

13. The compound of claim 1, or a tautomer thereof, or a pharmaceutically acceptable salt of each thereof, wherein ring B is pyridinyl optionally substituted with one substituent selected from the group consisting of halo, $C_1$-$C_6$ alkyl, $COR^{15}$, and $COOR^{15}$; wherein $R^{15}$ is $C_1$-$C_6$ alkyl optionally substituted with halo.

14. The compound of claim 1, or a tautomer thereof, or a pharmaceutically acceptable salt of each thereof, wherein ring B is pyridinyl.

15. The compound of claim 4, or a tautomer thereof, or a pharmaceutically acceptable salt of each thereof, wherein ring B is pyridinyl.

16. A pharmaceutical composition comprising a compound of claim 4, or a tautomer thereof, or a pharmaceutically acceptable salt of each thereof, and at least one pharmaceutically acceptable excipient.

17. A pharmaceutical composition comprising a compound of claim 8, or a tautomer thereof, or a pharmaceutically acceptable salt of each thereof, and at least one pharmaceutically acceptable excipient.

18. A method for increasing oxygen affinity of hemoglobin S in a subject, the method comprising administering to a subject in need thereof a compound of claim 4, or a tautomer thereof, or a pharmaceutically acceptable salt of each thereof.

19. A method for treating sickle cell disease, the method comprising administering to a subject in need thereof a compound of claim 4, or a tautomer thereof, or a pharmaceutically acceptable salt of each thereof.

20. A method for increasing oxygen affinity of hemoglobin S in a subject, the method comprising administering to a subject in need thereof a compound of claim 8, or a tautomer thereof, or a pharmaceutically acceptable salt of each thereof.

21. A method for treating sickle cell disease, the method comprising administering to a subject in need thereof a compound of claim 8, or a tautomer thereof, or a pharmaceutically acceptable salt of each thereof.

* * * * *

UNITED STATES PATENT AND TRADEMARK OFFICE
CERTIFICATE OF CORRECTION

PATENT NO. : 10,266,551 B2
APPLICATION NO. : 14/776717
DATED : April 23, 2019
INVENTOR(S) : Zhe Li et al.

It is certified that error appears in the above-identified patent and that said Letters Patent is hereby corrected as shown below:

On the Title Page

In the Inventors (item (72)) please replace "Zhe Li, South San Francisco, CA" with --Zhe Li, San Diego, CA--.

In the Claims

In Claim 1, Column 54, Line 45, please replace "hydrogen or $C_1$-C3" with --hydrogen or $C_1$-$C_3$--.

In Claim 1, Column 54, Line 51, please replace "wherein the C1-$C_6$ alkyl is" with --wherein the $C_1$-$C_6$ alkyl is--.

In Claim 8, Column 56, Lines 45-55, please replace

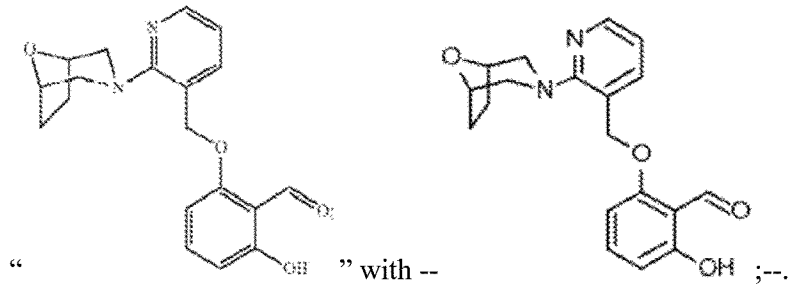

Signed and Sealed this
Twenty-third Day of May, 2023

Katherine Kelly Vidal
*Director of the United States Patent and Trademark Office*

CERTIFICATE OF CORRECTION (continued)
U.S. Pat. No. 10,266,551 B2

Page 2 of 2

In Claim 8, Column 56, Lines 56-66, please replace

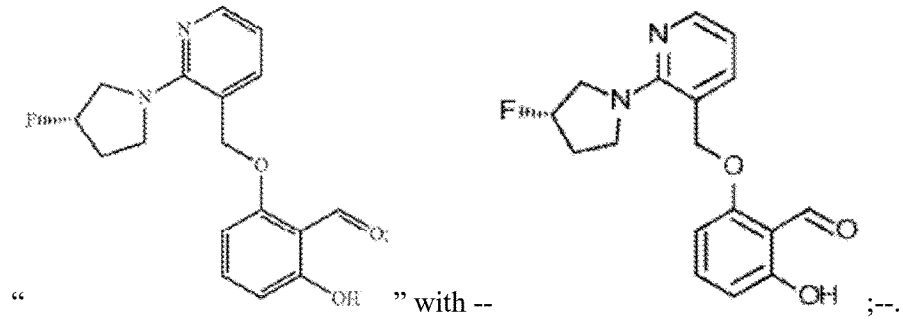

" " with -- ;--.

In Claim 8, Column 57, Lines 56-66, please replace

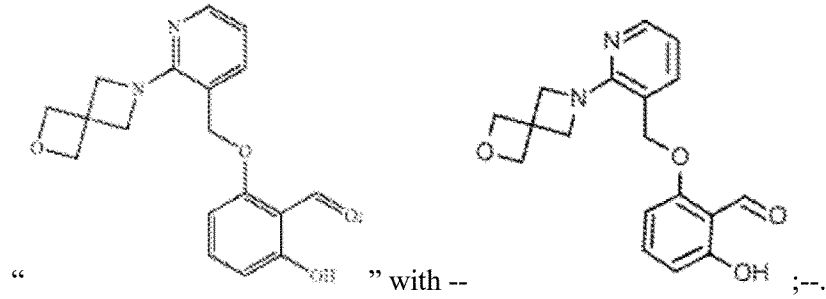

" " with -- ;--.